(12) United States Patent
Cosnier

(10) Patent No.: US 7,034,164 B1
(45) Date of Patent: Apr. 25, 2006

(54) ELECTRICALLY CONDUCTIVE POLYMERS CAPABLE OF BEING COVALENTLY GRAFTED ON BY LIGHT, METHOD FOR OBTAINING SAME AND USES AS SUPPORTS IN PROBES FOR SPECIFIC IDENTIFICATION IN ELECTRONIC BIOSENSORS

(75) Inventor: Serge Cosnier, Crolles (FR)

(73) Assignee: Universite Joseph Fourier, Grenoble Cedex (FR)

( * ) Notice: Subject to any disclaimer, the term of this patent is extended or adjusted under 35 U.S.C. 154(b) by 562 days.

(21) Appl. No.: 10/048,483

(22) PCT Filed: Aug. 7, 2000

(86) PCT No.: PCT/FR00/02267

§ 371 (c)(1),
(2), (4) Date: Aug. 14, 2002

(87) PCT Pub. No.: WO01/12699

PCT Pub. Date: Feb. 22, 2001

(30) Foreign Application Priority Data

Aug. 12, 1999 (FR) .................................. 99 10535
Nov. 29, 1999 (FR) .................................. 99 15022

(51) Int. Cl.
*C07D 207/30* (2006.01)

(52) U.S. Cl. ..................................................... 548/562
(58) Field of Classification Search .................. 548/562
See application file for complete search history.

(56) References Cited

U.S. PATENT DOCUMENTS 6,197,881 B1 * 3/2001 Cosnier ..................... 525/54.1

FOREIGN PATENT DOCUMENTS

| WO | 90/10655 | 9/1990 |
| WO | 95/29199 | 11/1995 |

OTHER PUBLICATIONS

XP-002139597 Derwent Publications Ltd., London, GB; JP 02 255716 A, Ricoh KK, Oct. 16, 1990.
XP-002139598 Derwent Publications Ltd., London, GB; JP 07 076572 A, Osaka Gas Co Ltd., Mar. 20, 1995.

* cited by examiner

*Primary Examiner*—Taofiq Solola
*Assistant Examiner*—Robert Shiao
(74) *Attorney, Agent, or Firm*—Dennison, Schultz, Dougherty & MacDonald

(57) ABSTRACT

The invention relates to new, inexpensive electropolymers capable of light-induced grafting, onto which specific identification probes can be easily grafted and having optimum capacity for interaction with the target analytes (DNA/$DNA_c$, PNA/$PNA_c$, enzyme/substrate/Antibody/Antigen).

These electropolymers capable of light-induced grafting are, for example, poly(pyrrole-benzophenone). Benzophenone forms sites for light-induced grafting.

The invention also covers the mono and oligomers which make up these novel electropolymers capable of light-induced grafting.

Another object of the invention is the process for their manufacture, as well as electronic biosensors containing these electropolymers capable of being grafted and/or grafted by probes for the analysis of biomolecules.

1 Claim, 15 Drawing Sheets

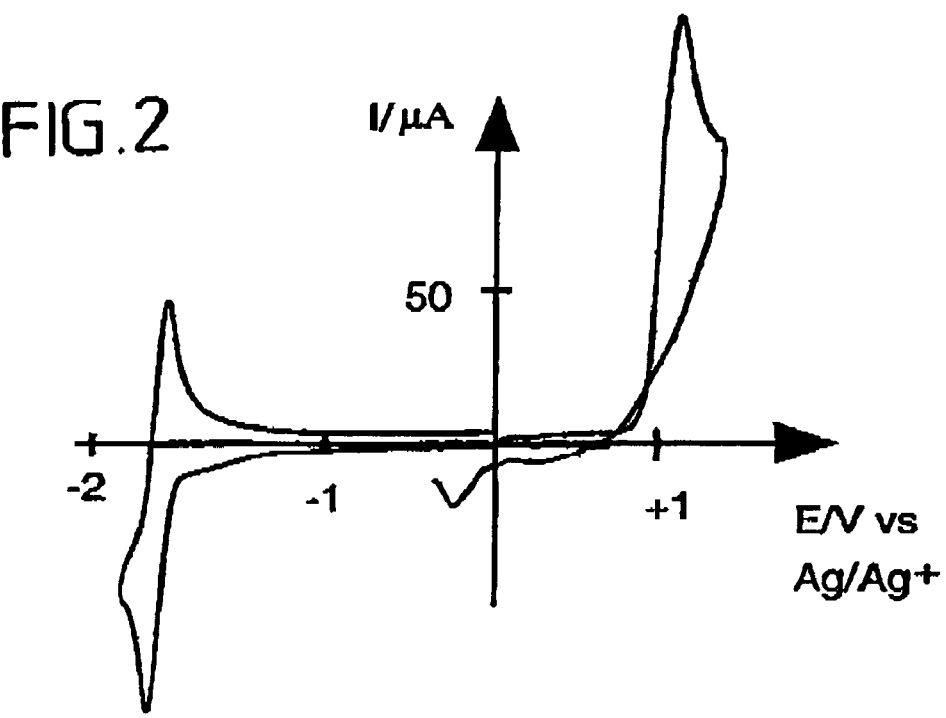
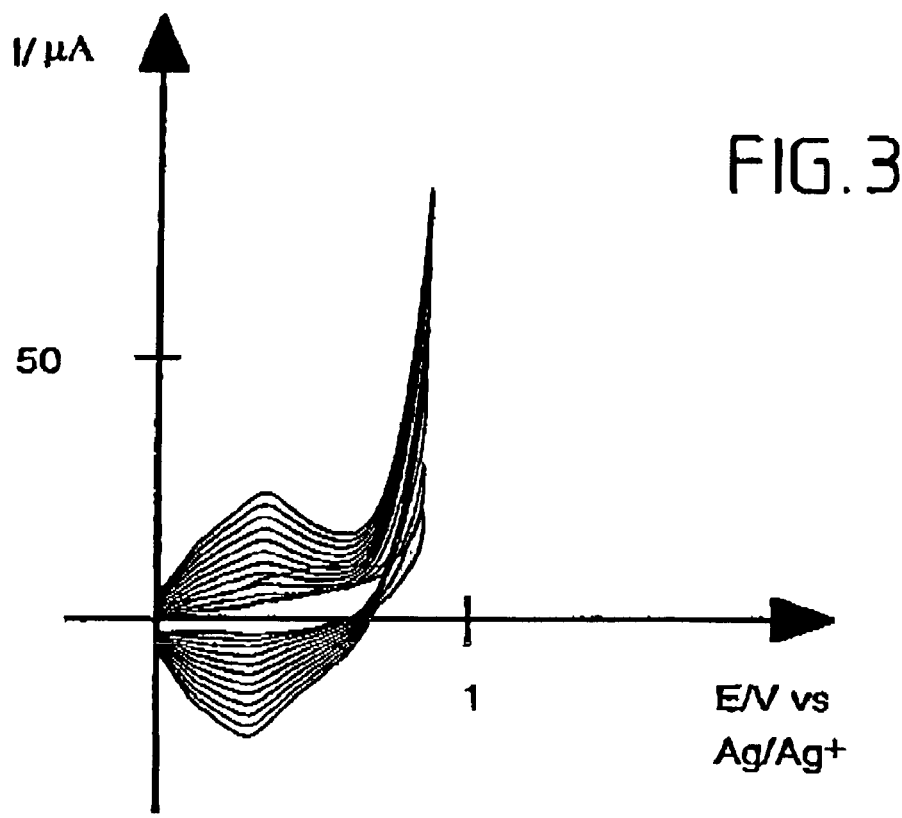

FIG.29
FIG.30
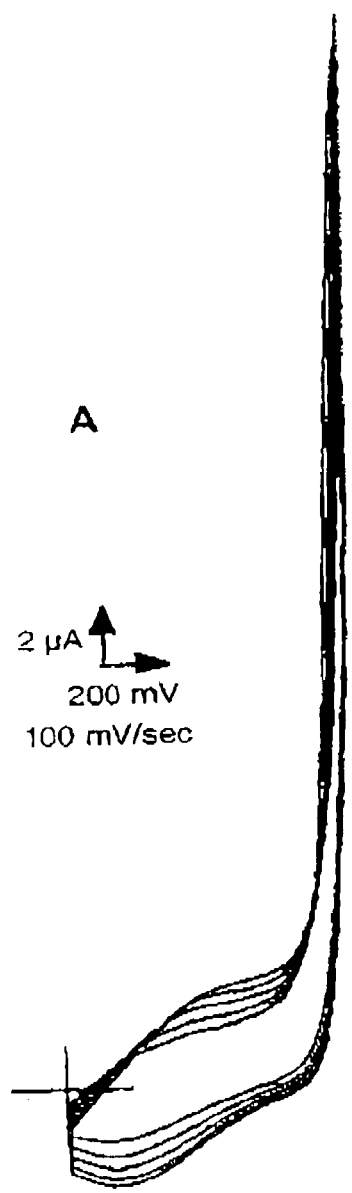
A
2 µA
200 mV
100 mV/sec
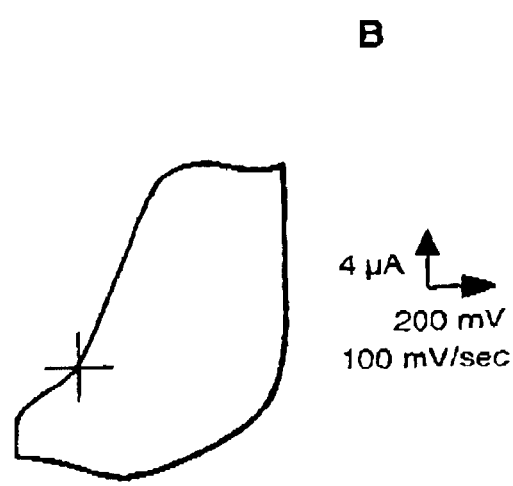
B
4 µA
200 mV
100 mV/sec

ELECTRICALLY CONDUCTIVE POLYMERS CAPABLE OF BEING COVALENTLY GRAFTED ON BY LIGHT, METHOD FOR OBTAINING SAME AND USES AS SUPPORTS IN PROBES FOR SPECIFIC IDENTIFICATION IN ELECTRONIC BIOSENSORS

The invention covers the field of electropolymers and, in particular, their application as constituent materials of biosensors and electroanalytical sensors.

This invention concerns polymers obtained by electropolymerisation, also called electropolymers, as well as a process for their preparation. Monomers and/or oligomers involved in this process are also covered by this invention. The invention also relates to the use of these electropolymers as anchoring supports for specific identification probes making up biosensors or electroanalytical sensors such as: (micro)electrodes, field-effect transistor sensors, biochips, semi-conductors, conductive fibre optics.

The combination of the specific molecular identification properties of biological macromolecules with the extreme sensitivity of optic, electrochemical or gravimetric sensors has led to the emergence of a new generation of analytical tools: the biosensors. In the last three decades, the development of biosensors has undergone huge expansion as a result of their potential industrial applications in the environmental field (on-site measurement of pollutants) and in biomedical analyses (portable or disposable biosensors, replacement of ELISA tests). Recently, the rapid growth of microelectronic technology has led to further opportunities in miniaturising biosensors. The principal objectives are implantable biosensors or combining several biosensors in order to obtain information about several analytes simultaneously. Microsensors can thus be manufactured by immobilising biomolecules on the surface of a wide variety of microtransducers such as microelectrode multiplots, interdigitated microelectrodes or field-effect transistors.

These biomolecules (oligo- or polynucleotides-DNA-RNA, enzymes, antibodies, antigens, peptidic nucleic acids, oligo or polypeptides) behave like specific identification probes, for example by interaction with the target biological substances to be analysed. Reference to biology to qualify the molecules concerned is not exclusive of other molecules analogous to molecules of biological origin in the strict sense of the term but can also include molecules manufactured by a synthetic chemical route (chimera).

The manufacture of biosensors is currently subject of fierce international competition, with biochips for DNA sequencing being the perfect illustration of this. The development of several thousand different oligonucleotide "spots" in perfectly localised positions on a flat support can be used to identify and quantify DNA or RNA functionalised by fluorescent markers.

Nevertheless, a technological block persists in the development of microbiosensors. Stable, reproducible and spatially controlled immobilisation of specific identification probes (for example oligonucleotides, peptidic nulceic polyacids or proteins) with biological properties completely retained remains a central problem. In effect, the majority of conventional procedures, such as reticulation, covalent grafting or trapping in gels or membranes suffer from the problem of low reproducibility and poor spatial resolution.

Other immobilisation techniques for probes, for example protein probes, have been developed using conventional printing technology such as screen-printing and ink-jet deposition. These allow the protein to be accurately localised. However, immobilisation by trapping the protein can reduce the accessibility of the protein and thus reduce the efficacy of specific interactions of the complementary oligonucleotide, antibody-antigen or enzyme-substrate type.

More recently, another method has involved controlled depositing of microvolumes (5 nl) containing the protein at specific points. The problems encountered with this approach are evaporation requiring the process to be conducted in a controlled-humidity atmosphere and problems of contamination from one deposit to another.

Photolithography of light-activated groups to immobilise biomolecules on supports contained in the microtransducers of biosensors is also an established technique.

The article by L. F. Rozsnyai, D. R. Benson, S. P. A. Fodor and P. G. Schultz, Angew. Chem. Int. Ed. Engl. 31 (1992) 759, describes covalent anchoring of antibodies on a silica support functionalised by light-activated groups of the benzophenone type. Functionalisation (or derivation) of substrates on silica is carried out using 3-aminopropyltriethoxysilane protected by t-butyloxycarbonyl(Boc) groups. After deprotection of the surface silane, an N-hydroxysuccinimide ester of 3-benzoylbenzoic acid is coupled to the surface silane. The antibodies to be grafted onto the support are then deposited and exposed, through a mask, to luminous radiation which activates, in uncovered areas, the bond attaching the immunoglobulin to the carbonyl groups of the benzophenones fixed to the support.

International patent application PCT WO 92/10092 describes an in situ technique for synthesis of an oligonucleotide network on a silane-containing substrate using 3-aminopropyltriethoxysilane and protected by a light-sensitive group of the 6-nitroveratryoxycarbonyl (NVOC) type. With this technique, localised deprotection of the substrate is achieved by exposure to light through a mask. The deprotected zone or zones then become the site of chemical coupling reactions of either nucleotides to each other to form oligonucleotides, or of nucleotides to the support to fix oligonucleotides synthesised ex-situ to head nucleotides as part of in situ synthesis of oligonucleotides.

In these photolithographic techniques for grafting probes to a support, geometric distribution of said probes is controlled by means of photomasks but the disadvantage of these techniques is the absence of any control of the depositing of light-activated groups on the support.

An alternative to these methods consists in immobilising specific identification probes, for example protein probes, by electropolymerisation of a monomer in the presence of the protein probe to be immobilised. This leads to the protein probe being trapped in electrogenerated polymer films. Localisation of probes can be spatially controlled by means of the possibilities offered by electrochemical targeting of the polymer film. An illustration of this is the article by Serge Cosnier (Can J. Chem. Eng., 76 (1998) 1000) which covers the manufacture of amperometric biosensors by entrapment in functionalised polypyrrole films. The electrochemical enzyme immobilisation procedure described in the article consists of two steps. The first step involves adsorption of an aqueous mixture of the enzyme and amphiphilic pyrrole onto an electrode surface while the second step is electropolymerisation of the adsorbed monomers.

Enzyme entrapment in electropolymers is also described in U.S. Pat. No. 5,286,364 which discloses electropolymerisation of 1,3-diaminobenzene and resorcinol. The enzyme immobilised in the electropolymer generated locally is glucose oxidase.

This entrapment technique for protein-based sensitive substances (probes) in electrogenerated polymers has the disadvantage of radically reducing accessibility to the immobilised substance. In particular, the steric constraints generated by the polymer surrounding the protein or oligonucleotide probes can hinder the formation of specific identification interactions of the antigen-antibody, enzyme-substrate or complementary oligonucleotide hybridisation type. As a result, electrochemical immobilisation of proteins or oligonucleotides has not been found to be the most suitable method for the manufacture of biosensors.

A slightly different approach consists in electrogenerating a polymer with groups likely to generate covalent binding to a protein. In this way, enzyme and oligonucleotides have been immobilised on polypyrroles by chemical grafting. However, these chemical reactions can denature sensitive probes (protein-polynucleotides).

A more promising strategy for fixing probes, for example protein or oligonucleotides probes, on electrogenerated films is immobilisation by means of affine systems which conserve the biological activity of proteins. According to this strategy, electrogeneration of a polymer film functionalised by biotine groups is carried out. Because of strong affine interactions between biotine (molecular weight=250 D) and avidine (molecule weight=66 000 D), an avidine monolayer forms spontaneously on the surface of the polymer by straightforward immersion of the support, a transducer in this case, in an avidine aqueous solution. Subsequent fixation of biotineylated probes (enzyme, antibody, antigen, oligonucleotides, peptidic nucleic polyacid) also takes place by straightforward immersion of the support, in this case a transducer, modified by avidine, in an aqueous solution of the probe substance chosen, the association constant between avidine and biotine groups being: $K_a=10^{15}M^{-1}$. Immobilisation of probes, for example protein probes, is thus carried out by non-denaturing anchorage conferring maximum accessibility on the protein.

The major inconvenience of this electroaffine method is the need for probes, especially proteins labelled with biotine groups, or probes, again especially proteins, conjugated with avidines.

The following articles are given as an illustration of these electroaffine techniques:

"Electrogeneration of biotineylated functionalised polypyrroles for the simple immobilisation of enzymes" S. Cosnier, B. Galland, C. Gondran and A. Le Pellec, Electroanalysis, 10 (1998) 808.

"Poly(pyrrole-biotine): a new polymer for biomolecule grafting on electrode surfaces", S. Cosnier and A. Le Pellec, Electrochim. Act, 44 (1999) 1833.

Electropolymers onto which sensitive probe substances are chemically grafted are also known. These electropolymers carrying chemically grafted probes can be used as a means for immobilising probes or markers in biosensors.

French patent FR-A-2 703 359 covers a polypyrrole type electrogenerated copolymer in which certain pyrrole monomers have been substituted by oligonucleotide lateral chains by means of aminoethyl spacing joints.

French patent FR-A-2 750 136 also covers grafted electrogenerated polypyrroles but, in this case, oligonucleotide grafts carry an active molecule (hormone: ACTH or biotine).

European patent application EP-A-314 009 discloses electrogenerated polymers of the polydithienylpyrrole type functionalised by enzymes such as glucose oxidase. Grafting of a functionalised group can be carried out by means of an amine (protected or not) carried by the pyrrole ring.

Application PCT WO 90/10 655 describes electropolymers of the polyacetylene-cis type grafted by enzymes of the glucose oxidase type via hydroxylated benzoquinone spacing joints. This PCT application also discloses electrogenerated polyanilines functionalised by reactive indicators of the glucose oxidase or enzyme corrector cofactor (FAD) type.

French patent application FR-A-2 720 832 covers electropolymers of the polythiophene, polypyrrole, polyphenylene, polythiophene-vinylene, polyaniline and polyacetylene type on which biologically active peptides are grafted in order to generate a specific interaction with chemical or biological entities of biological or medical benefit (hormones for example). This grafting is carried out chemically by means of an acetyl spacing arm attached to carbon atom no. 3 of the pyrrole ring. These grafted electropolymers can be used as electroactive membranes in biosensors.

All these known electropolymers onto which sensitive probe molecules are grafted present the disadvantage of requiring chemical processes likely to alter the probe molecules to be grafted. Moreover, it is difficult to control localisation of the grafts with these processes. Consequently, it is not possible to produce organised networks of the various specific identification probes which can be integrated into biosensors.

At the end of this review of the current state of the art, it can be seen that there is thus an acute need for a polymer support that can be used as a sensitive membrane in biosensors, keeping in mind that the specifications sought for such a membrane (or a sensitive membrane) are:

- to be able to carry sensitive specific identification probes immobilised in a reliable and lasting manner,
- to use an immobilisation method for sensitive probes that does not damage their capacity to interact specifically with the target molecules to be analysed,
- to be carriers of sensitive probes (for example proteins, oligonucleotides, peptidic nucleic polyacids . . . ) which are not denatured during the immobilisation process,
- to offer the possibility of easily controlling the localisation of probes such that probe arrays can be produced,
- that can be obtained in a simple and inexpensive manner such that they can be mass produced.

One of the central objectives of this invention is to make up for these shortcomings by providing new polymers onto which non-denatured specific identification probes can be easily grafted and which have an optimum capacity for reaction with the target analytes and whose localisation can be controlled, these new polymers also being of a low cost.

Another central objective of the invention is to provide new means of immobilising specific probes of the polynucleotide peptide, peptidic nucleic polyacid type allowing stable, inexpensive, non-denaturing and spatially-controlled immobilisation of probes.

Another central objective of the invention is to provide processes for the preparation of the above-mentioned electropolymers which can be used to make up immobilisation supports adapted to specific identification probes for electronic (micro)biosensors.

Another central objective of the invention is to provide new monomers from which the above-mentioned polymers can be obtained.

Another central objective of the invention is to provide method of fabrication of a biosensor using the preparation of the above mentioned electropolymers.

Another central objective of the invention is to provide an electronic biosensor whose sensitive membrane consists of the above-mentioned polymers onto which specific identification probes are grafted.

These objectives, amongst others, are achieved in this invention which primarily concerns new polymers obtained by electropolymerisation and characterised by the fact that they include groups that are light activated.

The electropolymers according to the invention can be prepared quickly and easily in the form of films with film thickness controlled precisely by means of the electric charge applied. These electropolymers can be deposited on many types of supports and, in particular, on small electrode surfaces of complex geometry.

More precisely, the electropolymers according to the invention are organic polymer films obtained by chemical oxidation or reduction, at the surface of an electrode, of monomers either adsorbed onto this surface or solubilised in an aqueous or organic electrolyte medium.

According to a preferred feature of the invention, these light-induced grafting polymers are chosen:

from the group of electrogenerated polymers: polyacetylenes, polyazines, poly(p-phenylene vinylidene), poly(p-phenylene), polypyrenes, polyfuranes, polyselenophenes, polypyridozines, polycarbazoles, polypyrroles, polythiophenes, polyindoles, polyanilines and their copolymers and/or the group of electrogenerated isolating polymers, preferably from the subgroup comprised of polyphenols, poly-(thiophenylenediamines), poly(dichlorophenolindophenol) and their copolymers.

The general formulae of polyacetylene, polypyrrole, polythiophene, polyaniline and polyindole are given below.

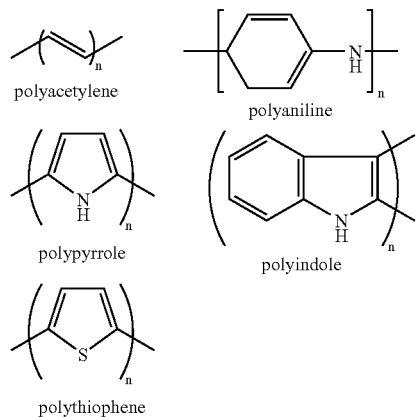

Electropolymers can only be formed on conductive or semi-conductive surfaces capable of transporting the electric charge required for polymerisation. This feature makes it possible to envisage electrochemical targeting. This means that by supplying certain zones of the conductive support, rather than others, with an electric current, polymer formation in the zones supplied can be circumscribed and thus lead to differentiated and independent zones each carrying a given grafted probe.

The light-induced grafting electropolymers according to the invention are suitable for simple, economic, reproducible and spatially controlled binding to specific identification probes which can be proteins, polynucleotides, peptidic nucleic polyacids or similar.

This type of immobilisation by light-induced grafting avoids the need for chemical reagents which might have a denaturing effect. Furthermore, the technique is straightforward since the probes do not have to be pre-treated or functionalised in order to be grafted. Finally, grafting can be carried out in a precise and rapid manner with the aid of photomasks.

With regard to light activated electropolymers according to the invention, it should be pointed out that said groups are preferably selected from the group including: diazoniums, phenylazides, azobenzes, benzophenone derivatives and combinations of these groups.

In accordance with the invention, benzophenone is a particularly preferred light-activated group.

In general, the term light-activated group, in the sense of the invention refers to a chemical group which is converted by irradiation into a highly active compound likely to form a covalent bond with other compounds in solution in an organic or aqueous medium.

The number of light-activated groups in the electropolymers according to the invention is a parameter which allows them to be typified.

It is therefore particularly advantageous, according to the invention, that at least 0.01% by number of these constituent (co)monomers, preferably at least 10% of these constituent (co)monomers, and more preferably still each of these constituent (co)monomers, carries at least one group that can be activated by light.

Naturally, the electropolymers according to the invention can be either homopolymers or copolymers.

These copolymers can be of the block or static type.

According to an advantageous aspect of the invention, the light-induced grafting electropolymers of the invention have a degree of polymerisation $DP_n$ between 200 and $10^7$, preferably between $10^3$ and $10^7$ and more preferably still between $10^4$ and $10^7$.

These electropolymers can also be defined by the number of immobilised monomeric molecules per surface unit which is preferably between $10^{-11}$ and $10^{-6}$ mole cm$^{-2}$ and, more preferably still, between $5 \times 10^9$ and $10^{-8}$ mole.cm$^{-2}$. The thickness of the polymer film at $10^{-6}$ mole.cm$^{-2}$ is between 0.2 and 2 μm.

The electrochemical properties of the polymers of the invention are another means of defining them. It is therefore cyclic voltammetry reveals that the electropolymers according to the invention have a reversible signal characteristic of a redox system whose voltge value is advantageously less than or equal to 0 volt, preferably less than or equal to −1 volt and more preferably still between −1.5 and 2.5 volt. This signal results from the presence of the light-activated group. Moreover, these polymers can be electronic conductor polymers. In this case, the amount of polymer electrogenerated on a conductive support can be determined by integration of the electric charge corresponding to electroactivity of the polymer in the potential range between −1V and +1V.

Voltammetric measurement is carried out by potential sweeping between the limit values, for example 0 and −2.5 volts. The liquid conducting medium consists, for example, of CH$_3$CN+TBAP 0.1M. Measurement of voltage is carried out with reference to Ag/Ag$^+$10 mM in CH$_3$CN.

According to a preferred embodiment of the invention, the electropolymers it relates to carry a light-activated group on each of their constituent monomers.

The light-activated groups can be identical or different on the same polymer chain and/or another polymer chain. In accordance with a preferred mode of application, the light-activated groups are identical on all polymer chains.

Below a $DP_n$ in the order of 50, the electropolymers according to the invention are preferably called "oligomers".

With regard to their preparation, the preferred process according to the invention is characterised in that it essentially consists of:
- using at least one type of electropolymerisable monomer;
- fixing at least one light-activated group to at least part of the (co)monomers used
- electropolymerising the (co)monomers, electropolymerisation preferably taking place on a conductive support by subjecting (co)monomers to potential sweeping and/or imposed-potential electrolysis (chronoamperometry) or to a constant current (chronopontentiometry).

Depending on whether homo- or copolymers are required, identical monomers or comonomers belonging to at least two different species are used.

In a particularly preferred mode of preparation, electropolymerisation of monomers or comonomers, whether or not functionalised by at least one light-activated group, is carried out on a conducting support so as to form an electropolymer film over the entire zone exposed to the electric field.

For a given electropolymerisation support, it is perfectly acceptable only to supply certain select zones with an electric current of the conducting support. In this way, electrochemical targeting takes place which allows the light-induced grafting electropolymer to be localised at extremely precise points.

Advantageously, the copolymerisable (co)monomers used are selected from:
- the subgroup of conducting (co)monomers including:
  acetylene, pyrroles, thiophenes, indoles, anilines, azines, p-phenylenevinylenes, p-phenylenes, pyrenes, furanes, selenophenes, pyrridazines, carbazoles and their mixtures,
- and/or the subgroup of isolating (co)monomers including the phenols, ortho-phenylenediamine, dichlorophenolindophenol and their mixtures.

Advantageously, groups that can be light activated are selected from among the group made up of diazoniums, phenylazides, azobenzenes, benzophenone derivatives and combinations of these groups.

In terms of methodology, several procedures are possible according to the invention. The grafting step can therefore take place before, during or after the electropolymerisation step.

In a preferred embodiment of the process, substitution of light-activated groups on all starting monomers is carried out prior to electropolymerisation. The latter involves (co)monomers each conjugated to at least one group, preferably light-activated group.

According to one variant, electropolymerisation of monomers not substituted by the light-activated groups can also be carried out, with substitution only performed in the finished polymer.

Naturally, the two variants described can be combined.

The solution consisting of simultaneously carrying out electropolymerisation and substitution of light-activated groups is certainly not the preferable route but cannot be excluded from the invention.

Electropolymerisation is preferably carried out using monomers but it is also possible to use oligomers, whether or not functionalised by light-activated groups, as the starting products of electropolymerisation in combination or not with (co)monomers.

Electropolymerisation is advantageously carried out in practice under room pressure and temperature conditions.

The support used can be for example metal electrodes (gold, platinum, stainless steel), glassy carbon or graphite electrodes, transparent electrodes (glass or quartz coated with a gold film, $TiO_2$ or $O_2$), volume electrodes such as carbon felts, carbon powder or graphite, woven metal sheets such as stainless steel or $TiO_2$ nanoporous gels.

A liquid medium consisting of a solution, a suspension or an emulsion of (co)monomers, and possibly oligomers, in aqueous or organic solution is added to the support. The support then undergoes repeated potential sweeping (for example between −0.5 V and 1.2 V). The support zones supplied in this way are the site of formation of an electropolymer film on the surface.

The presence of an electropolymer film can be characterised by cyclic voltammetry.

The electropolymer obtained is substituted by suitable light-activated groups which allow light-induced grafting of sensitive molecules or specific identification probes, notably by affine interaction. The degree of substitution with light-activated groups allowing photoanchorage of is between 0.01 and 100%.

According to another aspect, the invention relates, in terms of a new industrial product, to a monomer which can be incorporated into the above-described electropolymers and/or used in the preparation process of these electropolymers. The new monomer is characterised by the fact that it includes at least one electropolymerisable entity and at least one light-activated group.

The electropolymerisable entity is selected from:
- The conductive co(monomer) subgroup including:
  acetylene, pyrroles, thiophenes, indoles, anilines, azines, p-phenylenevinylenes, p-phenylenes, pyrenes, furanes, selenophenes, pyrridazines, carbazoles and their mixtures,
- and/or the subgroup of isolating (co)monomers including the phenols, ortho-phenylenediamine, dichlorophenolindophenol and their mixtures.

Advantageously, the light-activated group is selected from the group including: diazoniums, phenylazides, benzophenone derivatives and combinations of these groups.

This invention also covers, as a new industrial product, oligomers that can be used in the process described above, wherein said oligomers include one or more monomers as described in the paragraph above.

The electropolymers, (co)monomers and oligomers presented above having the property of undergoing light-induced grafting constitute other new and inventive objects when they include elements grafted on by means of their light-activated groups. From this follows that the invention covers polymers, monomers and oligomer characterised in that they include substituents grafted by light obtained by reacting one or more substances with their groups capable of being activated and grafted by light, these substances preferably chosen from among biological (macro)molecules and/or chimera of these and/or units of these (macro)molecules and/or these chimera.

Examples of light-induced graft substances are amino acids, oligopeptides, polypeptides, proteins, glucoproteins, lipoproteins or nucleotides and oligonucleotides, RNA or DNA type polynucleotides, of biological or synthetic origin, enzymes, coenzymes and vitamins.

Examples of biomolecule chimera are peptidic nucleic (poly)acids, enzyme prosthetic sites such as metalloporphyrines, isobacteriochlorines, corrines, chlorines, artificial antibodies based, for example, on the polymer to be imprinted.

According to other advantageous aspects of the invention, the invention also covers:
- polymers, monomers, or oligomers wherein the above-cited light-induced grafting biological (macro)molecules are chosen from the group consisting of amino acids, oligopeptides, polypeptides, proteins, glucoproteins, lipoproteins or nucleotides and oligonucleotides, RNA or DNA type polynucleotides of biological or synthetic origin, enzymes, coenzymes and vitamins. The above-cited biomolecule chimera are selected from among the group comprised of peptidic nucleic (poly) acids, enzyme prosthetic sites such as metalloporphyrines, isobacteriochlorines, corrines, chlorines, artificial antibodies based, for example, on the polymer to be imprinted.

a pyrrolbenzophenone monomer of formula:

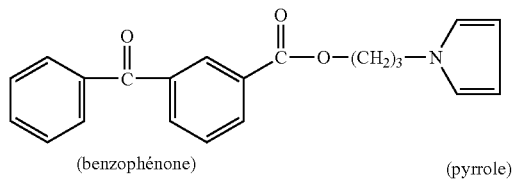

in particular obtained by reacting 3-benzoylbenzoic acid with 3-pyrrol-1-propanol, a 4-(2-aminoethyl)phenol-benzophenone monomer of formula:

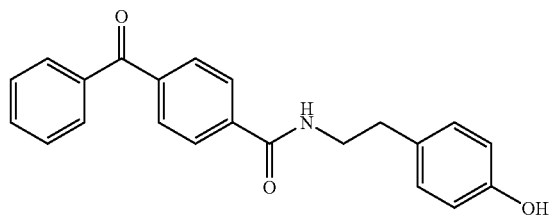

in particular obtained by reacting 4-(2-aminoethyl)phenol with 4-benzoylbenzoic acid, an indol-benzophenone monomer of formula:

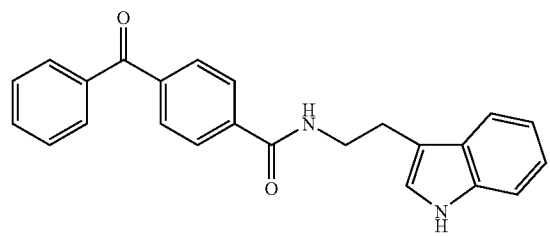

in particular obtained by reacting 3-(2-aminoethyl)indole with 4-benzoylbenzoic acid, a vinylaniline-benzophenone monomer of formula:

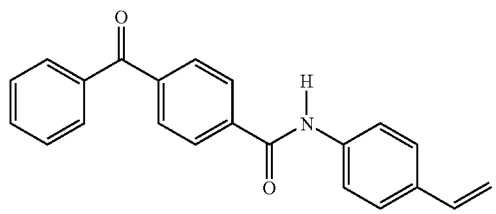

in particular obtained by reacting vinylaniline with 4-benzoylbenzoic acid, an azidophenylpyrrole monomer of formula:

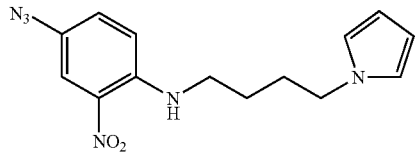

in particular obtained by reacting 4-fluoro-3-nitro-phenylazide with aminobutylpyrrole, a light-induced grafting electropolymer characterised in that it is prepared from a monomer such as that defined in the preceding description or the following description, particularly with reference to the examples, or from an oligomer such as that defined in the preceding description or the following description, particularly with reference to the examples, a poly(pyrrolbenzophenone) obtained from the above-mentioned pyrrole-benzophenone, preferably with a light-induced grafting substance such as that defined in the description and claims, better still chosen from a protein, preferably bovine or human serum albumin, an enzyme, preferably glucose oxidase, a biotine, preferably the avidine-biotine affine system, thionine, an antibody, preferably rabbit antibody (IgG), a polyphenol-benzophenone polymer obtained from the above-cited phenol-benzophenone monomer, preferably grafted with a light-induced grafting substance such as that defined in the description and claims, better still chosen from an enzyme, preferably glucose oxidase, a poly-indol-benzophenone polymer obtained from the above-cited indol-benzophenone monomer, preferably grafted with a light-induced grafting substance such as that defined in the description and claims, a polyvinyl-benzophenone polymer obtained from the above-cited vinylaniline-benzophenone monomer, preferably grafted with a light-induced grafting substance such as that defined in the description and claims, a polypyrrol-phenylazide polymer obtained by photopolymerisation from the above-cited phenylazide-pyrrole, preferably grafted with a light-induced grafting substance such as that defined in the description and claims, better still chosen from an enzyme, preferably glucose oxidase.

According to another of its aspects, the invention relates to a process for the manufacture of electronic biosensors of the type incorporating at least one (micro)transducer including at least one sensitive membrane carrying identification probes specific to the target molecules to be analysed, wherein the sensitive membrane is fixed on the transducer support by means of at least one polymer such as that described above, and wherein the specific identification probes are grafted onto light-activated groups of the polymer by means of light-induced activation.

These biosensors or these biosensor elements can be (micro)electrodes, semi-conductive devices such as field-effect transistors or even interdigitated microelectrode networks, microscale quartz, micometric or nanometric carbon or graphite fibres, optic fibres coated with a conducting layer.

These (micro)conductors are suitable for use as supports for the development of the light-induced grafting electropolymers according to the invention. Once the desired areas of the electropolymer is formed on the microtransducer, light-induced grafting commences. To this end, the electropolymer film is irradiated, for example using a 300–400 nm lamp (as a function of the light-activated group in question) in the presence of molecules or biomolecules (specific identification probes). The molecules or biomolecules to be grafted are applied in the form of a suspension, dispersion or in solution in an organic or aqueous medium, as an emulsion or dissolved in micellae or inverse micellae.

Irradiation devices are well known means. It is thus perfectly possible to envisage carrying out continuous irradiation in a tunnel on an industrial scale.

This invention also relates to an electronic biosensor of the type comprised of at least one (micro)transducer including at least one sensitive membrane carrying identification probes specific to the target molecules to be analysed, wherein the sensitive membrane includes at least one polymer as described above onto which are grafted by light (preferably in a localised manner) substituents which correspond to specific identification probes.

The microtransducers on which biomolecules are immobilised using the electropolymers of the invention can be microelectrodes, interdigitated microelectrodes, field-effect transistors, biochips notably for DNA and RNA or protein sequencing.

These biochips can be in the form of matrix networks of specific identification probes consisting of, for example, oligonucleotides fixed locally to isolating/semi-conducting structures, functioning on the principle of a field effect, for example.

The technology according to the invention is particularly well-adapted to the manufacture of this type of sensor because of the possibility of spatial control of probe fixation by electrochemical targeting and because of the simplicity of grafting molecules by light activation and photomasking.

Optic or electric immunosensors as well as microscale quartz can be given as other examples of biochips.

Finally, the invention relates to a support forming the electrode wherein this includes at least one layer of a polymer such as that defined in the description and claims.

This invention will be better understood in the light of the following examples which describe the process for obtaining light-induced grafting electropolymers and their characterisation, grafting of proteins onto said electropolymers and characterisation of the grafted products obtained. These examples will also clarify all the advantages and variants of the invention.

EXAMPLES

DESCRIPTION OF FIGURES

FIG. 2 is a graph giving the electrochemical characterisation of the monomer obtained in example 1.1, i.e. pyrrole-benzophenone.

FIG. 3 is a voltammogram illustrating electropolymerisation of the monomer in example 1.1 pyrrole-benzophenone.

FIG. 9 (graph A) the electrochemical signal of the polypyrrole-benzophenone film, without light excitation, before soaking in 0.5 mM thionine in solution in acetonitrile, whereas the graph after soaking or immersion in this solution is represented by graph B FIG. 10.

FIG. 29 represents (graph A) the electrode line immersed in 4-fluoro-3-nitro-phenylazide-aminobutylpyrrole solution synthesised in example 8.2, polymerised by repeated potential sweeping between 0 and 0.90 V/Ag/Ag$^+$, showing polymer formation by the appearance and development of a redox system at +0.4 V/Ag/Ag$^+$ characteristic of the electroactivity of polypyrrole chains.

FIG. 30 represents (graph A) the signal for the electrode described in the experiment in FIG. 29 after 2 mC electro-oxidation and transfer to a monomer-free electrolyte solution.

Section I—Preparation of Monomers and Polymers Capable of Being Covalently Grafted by Light to Benzophenone Groups 1.1—Pyrrole Benzophenone Monomer (benzophénone)   (pyrrole)

This monomer is prepared as described bellow:

Reaction of pyrrole alcohol with 3-benzoyl-benzoic acid in the presence of DMAP.

According to a currently preferred embodiment, 3-benzoylbenzoic acid is reacted with 3-pyrrole-1-propanol in the presence of a catalytic amount of dimethylaminopyrridine or DMAP and preferably in the presence of an activating agent such as dicyclohexylcarbodiimine.

The synthesis reaction is carried out as follows:

425 mg of 3-benzoylbenzoic acid (2 mmoles) and 413 mg of dicyclohexylcarbodiimine (2 mmoles) are dissolved in 20 ml of dichloromethane and left for 5 min. 208 mg of 3-pyrrole-1-propanol (1.66 mmole) are added to the reaction mixture and stirred for 5 minutes. A catalytic amount of dimethylaminopyrridine or DMAP (81 mg, 0.66 mmole) is then added. The reaction mixture is maintained at about 20° C. with stirring for 48 hours.

After addition of water and extraction of dichloromethane, the organic solution is evaporated under pressure.

The residue is then dissolved in ethyl ether and the solution obtained is filtered in order to eliminate insoluble products. After evaporation of the solvent, the product is chromatographied on a silica column with dichloromethane as the eluent.

After chromatography, the purity of pyrrole-benzophenone was tested by NMR and mass spectrometry. H NMR (CD Cl$_3$) S (ppm) 2.20 (m, 2H), 4.1 (t, 2H), 4.29 (t, 2H), 6.10 (t, 2H), 6.60 (t, 2H), 7.52 (m, 4H), 7.80 (d, 2H), 7.98 (d, 1H), 8.22 (d, 1H), 8.40 (s, 1H).

Mass spectrometry by electronic impact: 333 (100%), 209 (14%), 152 (11%), 124 (21%).

Figure 1:
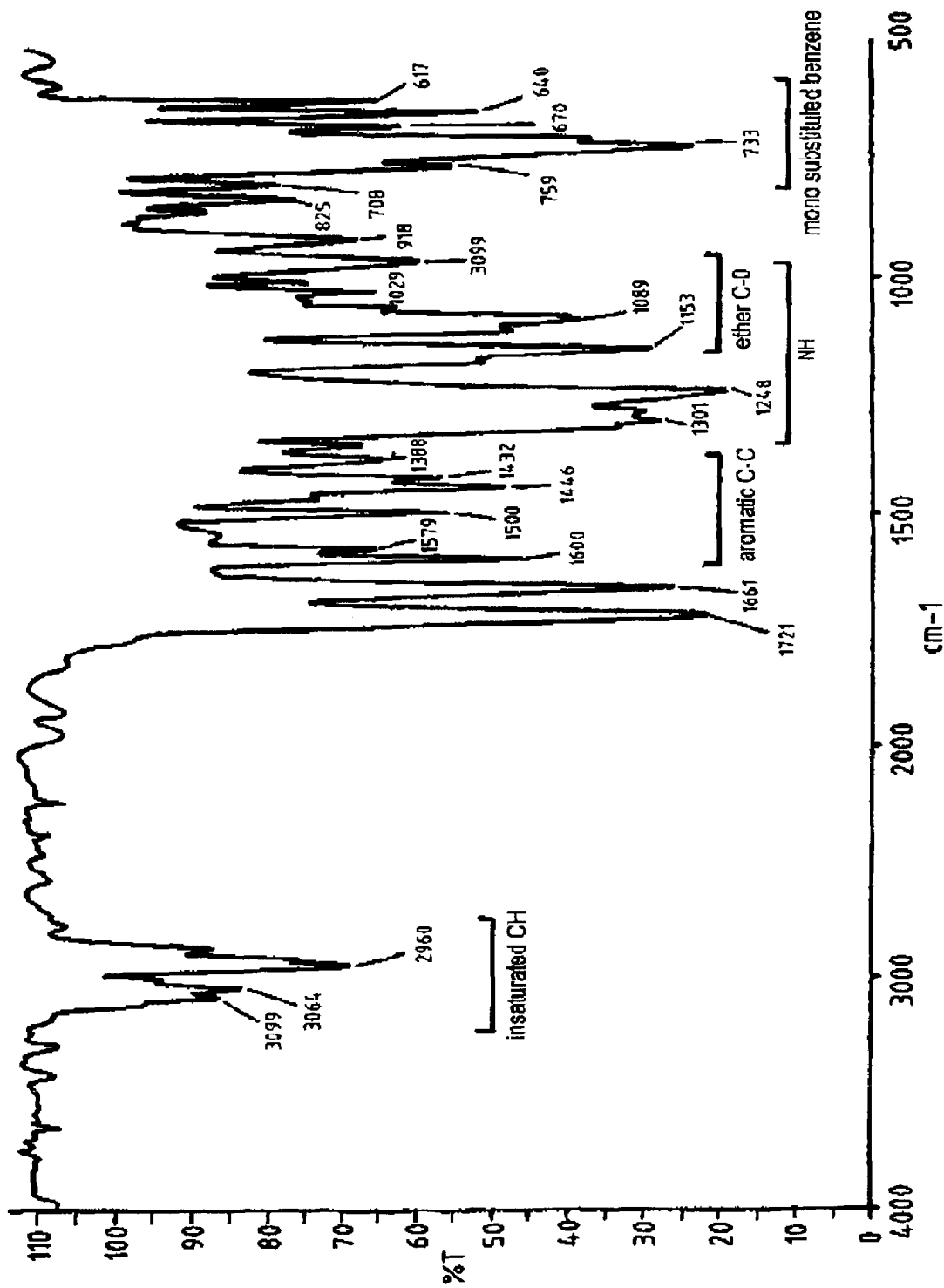
FIG. 1 represents the spectrum obtained by infrared spectroscopy (IR) of the pyrrole-benzophenone monomer in its liquid form plotted in transmission mode.

The spectrum was recorded by infrared spectroscopy (IR) of the pyrrole benzophenone monomer in its liquid form using a specular reflection device in transmission mode which is shown in FIG. 1, in this case a specular reflection device available under the trade name Perkin-Elmer Spectrum GX FT IR System capable of functioning in either transmission or specular reflection mode.

The electrochemical properties of this product were analysed by cyclic voltammetry.

As shown in FIG. 2 appended above, pyrrole benzophenone is irreversibly oxidised at 1.06 V vs Ag/Ag$^+$10 mM in CH$_3$CN. Irreversible oxidation of this monomer consists in the formation of a radical pyrrole cation, the 1$^{st}$ step in the polymerisation phenomenon leading to the polypyrrole.

These pyrrole radicals bind to each other to give covalent bonds and release protons into the electrolytic medium. This proton release is seen during return sweeping by the appearance of an irreversible cathode peak at about −200 mV (FIG. 2). This peak corresponds to reduction at the surface of the platinum electrode of protons released during the pyrrole-benzophenone polymerisation process. After coupling of the two pyrrole radicals and loss of protons leading to rearomatisation of the dimer, the latter acts in a manner similar to a pyrrole-benzophenone cation radical. A polypyrrole chain is thus generated by continuous electrochemical propagation and results in an insoluble polymer. As the anion radical is stable, benzophenone is reversibly reduced by 1 electron in a protein-free medium. Effectively, in the cathode area, a reversible signal at −1.96 V (FIG. 2) corresponding to monoelectric reduction of pyrrole-benzophenone is observed.

Example 2

Electropolymerisation 2.1—Obtaining poly(pyrrole benzophenone)

Repeated potential sweeping between 0 and 0.86 V leads to the formation of a pyrrole film on the electrode's surface. This can be seen from the appearance and development of a redox system at +0.32 V characteristic of the electroactivity of polypyrrole chains (cf FIG. 3 Electropolymerisation of pyrrole benzophenone 3.6 mM in CH$_3$CN+0.1 M TBAP).

Formation of the poly(pyrrole benzophenone) film at the surface of the electrode is advantageously carried out at constant potential equal to 900 mV/Ag/Ag$^+$.

Figure 4:
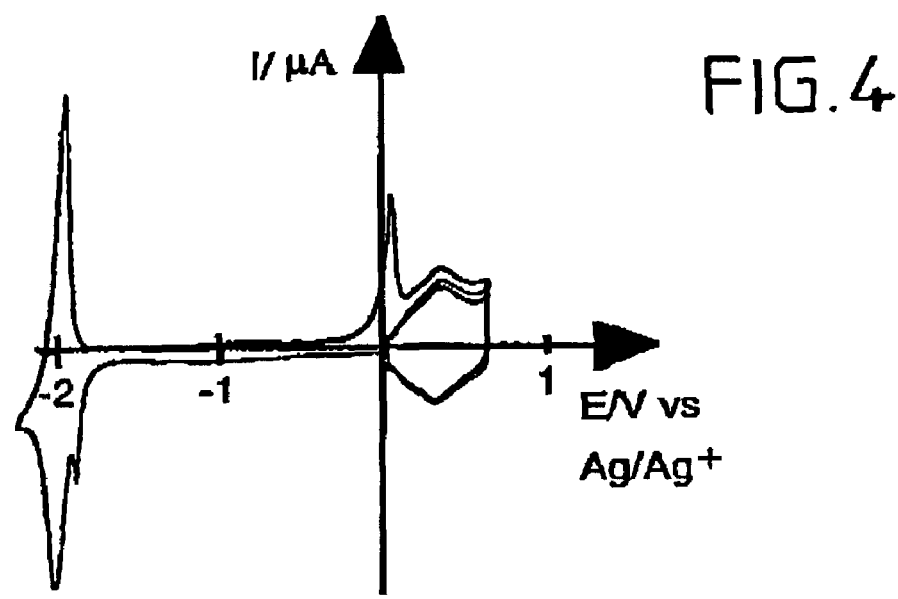
FIG. 4 is a cyclic voltammetry graph obtained from the electrode coated with poly(pyrrole-benzophenone) light-induced grafting electropolymer obtained in example 2.
Figure 5:
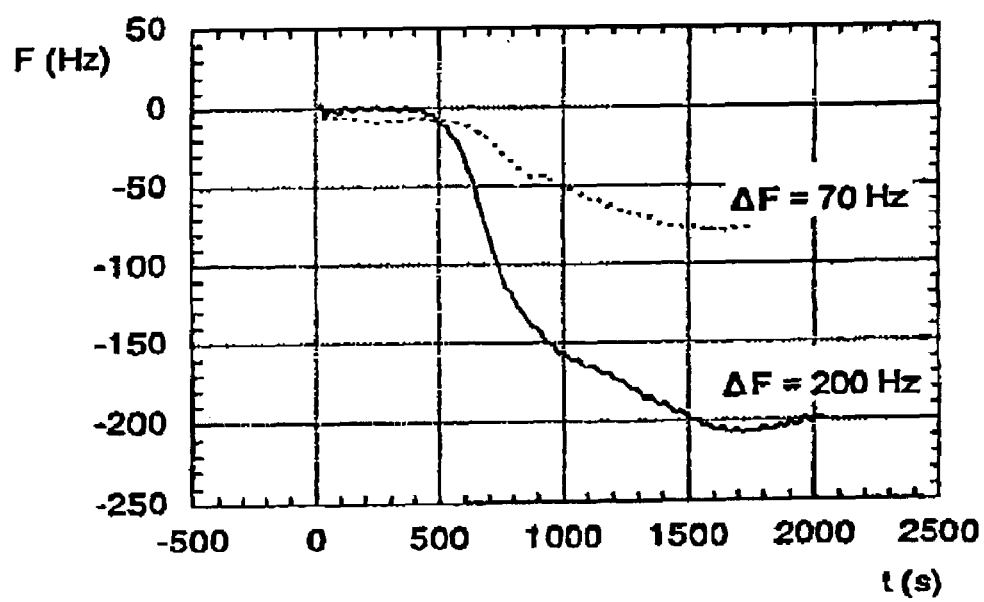
FIG. 5 shows 2 graphs representing the change in frequency F (Hz) as a function of time t (Δ), this change resulting from immobilisation of avidine (example 3.2) on microscale quartz modified by poly(pyrrole-benzophenone) films and previously contacted with a biotine aqueous solution with irradiation (—) and without irradiation (----).

After transfer of the electrode to a monomer-free electrolyte solution, the voltammogram of this electrode shows the typical electroactivity of polypyrrole films in the anode region. Moreover, the reversible signal for the reduction of benzophenone groups at E$_{1/2}$=−1.96 V confirms the presence of a polymer film at the surface of the electrode (cf. FIG. 4 : Voltammetry of the electrode after polymerisation) as well as the presence of light-activated groups in this polymer.

Inclusion of the charge relative to oxidation of the polypyrrole chains makes it possible to calculate the amount of polymerised monomer at the electrode surface. Proceeding in this manner, a poly(pyrrole benzophenone) film corresponding to $1.8 \times 10^{-8}$ mole.cm$^{-2}$ is obtained.

2.2—Infrared Spectroscopy Showing that a poly(pyrrole benzophenone) Film is Obtained The poly(pyrrole benzophenone) films obtained in step 2.1 above by electrochemistry are characterised by infrared spectroscopy (IR), using the above-mentioned specular reflection device. This method is adapted to the analysis of surface layers as the degree of light reflected depends on the roughness of the surface and the absorption properties of the sample.

It should be recalled that to observe the changes caused by polymerisation, the IR spectrum of the monomer in liquid form was first plotted in transmission mode and shown in FIG. 1.

the formation of a covalent bond. This photolysis process, which takes place at 350 nanometres (nm), has been widely observed in solution.

The efficacy of light-induced grafting onto poly(pyrrole benzophenone) films was identified by electrochemistry in this invention.

3.1.—Grafting of an Electroactive Species: Thionine

The tips of glassy carbon coated with a film of polypyrrole benzophenone (PP BP) formed by the passage of 0.2 mC (millicoulomb) were used. These tips were immersed and irradiated for two hours by a 250 W mercury lamp through an IR filter with an intensity of 100 mWcm-2. Light irradiation between 300 and 350 nm was carried out in a 1 mM thionine organic solution, previously deoxygenated by argon bubbling for 30 minutes.

The principle of the reaction method is given below:

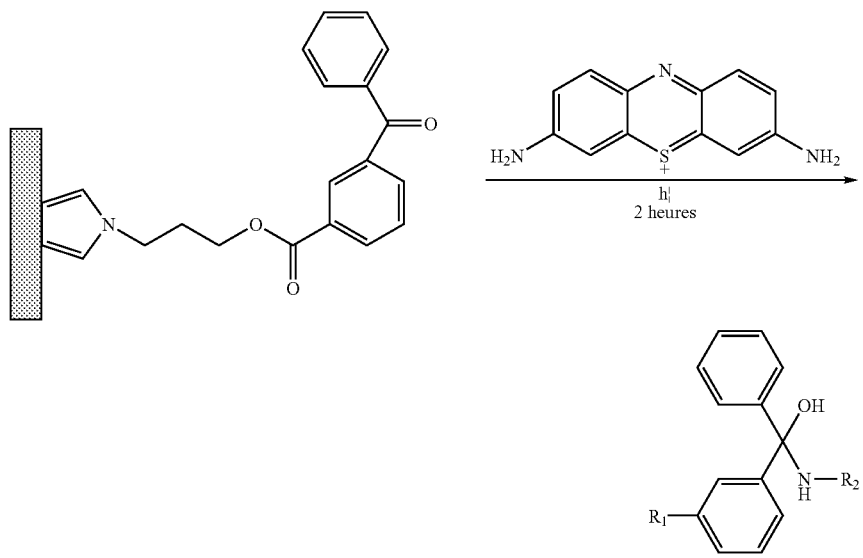

Figure 6:
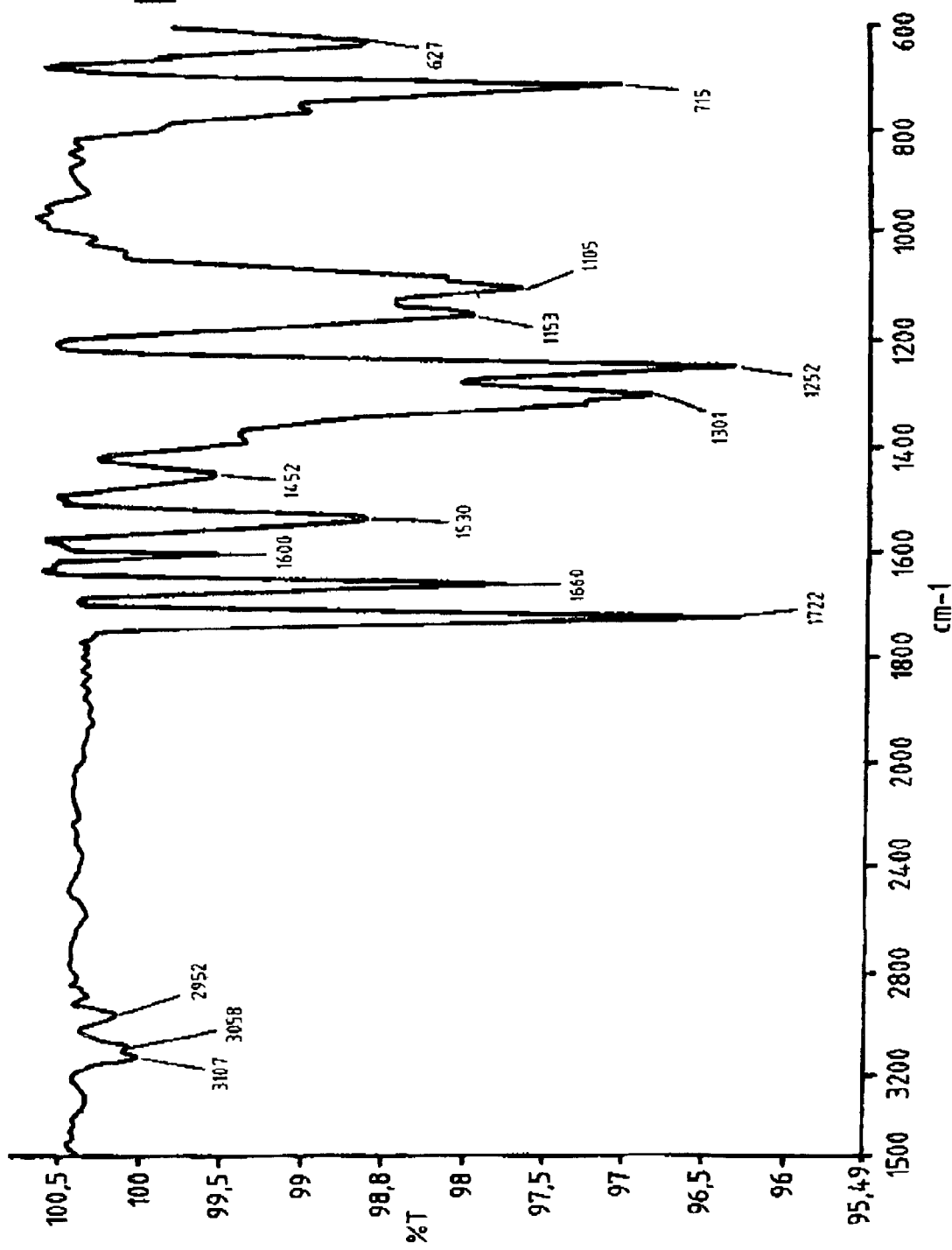
FIG. 6 represents the infrared spectrum of the pyrrole-benzophenone polymer film obtained from the monomer whose IR spectrum is given in FIG. 1.

The infrared spectrum of the poly(pyrrole benzophenone) polymer film is shown in FIG. 6 in specular reflection mode.

A comparison of FIGS. 1 and 6 shows that as a result of using two different methods, in other words transmission in FIG. 1 and specular reflection in FIG. 6, and changes in product state, respectively liquid and film, the spectrum in FIG. 6 is much less dense and the intensity of the rays obtained is much diminished. This reproducible spectrum shows that the film, once formed, retains the functional groups necessary for light-induced grafting.

Example 3

Figure 7:
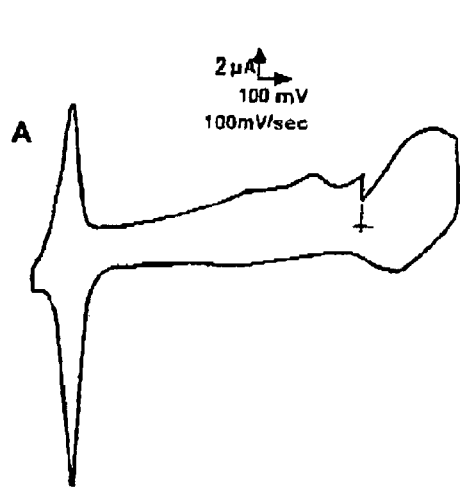
FIG. 7 represents (graph A) the electrochemical signal for the polypyrrole-benzophenone polymer film whose infrared spectrum is given in FIG. 6.
Figure 8:
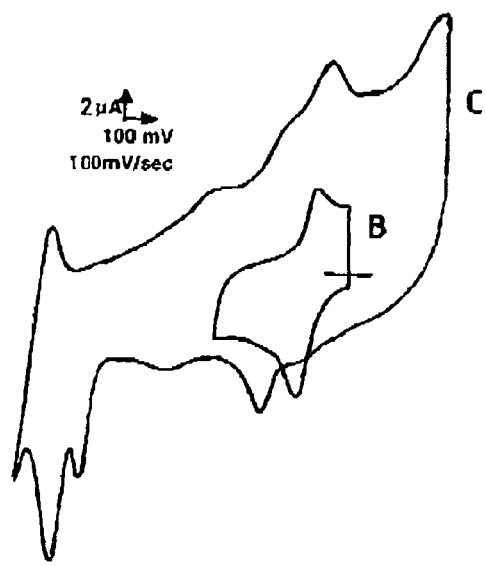
FIG. 8 represents (graph B) the electrochemical signal recorded with an uncoated electrode by potential cycling in 0.5 mM thionine in solution in acetonitrile while the graph after soaking or immersion in this solution is represented by graph C in FIG. 8.

Light-Induced Grafting of Biomolecules onto the Electrically Conductive Polymers of Example 2 Capable of Being Grafted on by Light Identification of Light-Induced Grafting of Different Aminated Species The benzophenone functional group is known to be the precursor of the light-induced generation of the ketone biradical. These biradicals are hydrogen acceptors and detachment of a proton from the target molecules precedes The electrochemical signal of electrodes in acetonitrile was recorded before and after grafting. Graph A in FIG. 7 represents the electrochemical signal of the film before grafting of the electroactive species. Graph B in FIG. 8 shows the signal recorded with a bare tip by potential cycling in 0.5 mM thionine in solution in acetonitrile. Graph C of FIG. 8 shows the electrochemically signal after grafting on by light of the electroactive species.

The appearance of a practically reversible signal for thionine reduction on the voltamperogram of the modified electrode shows the presence of the species in the film. In fact, electrochemical reduction of thionine can only take place at the surface of the electrode then propagate by electron jumps between immobilised thionine sites.

The same experiment carried out without light excitation of the immersed tips (blank) does not lead to any significant change in the electrochemical signal of the polymer film.

Figure 9:
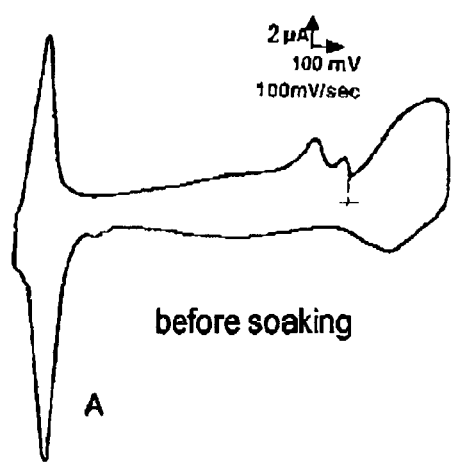
FIGS. 9 and 10 show the following.
Figure 10:
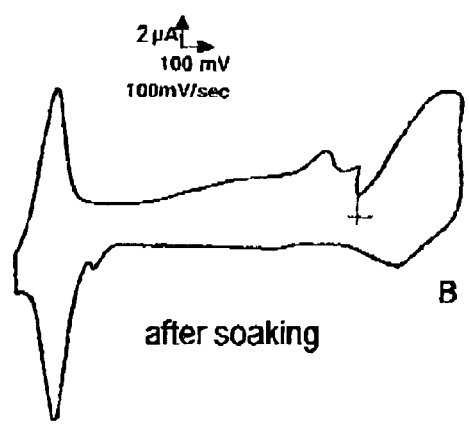

Graph A obtained prior to soaking is shown in FIG. 9 and graph B obtained after soaking or immersion is shown in FIG. 10.

The reversible signal for reduction in benzophenone groups is slightly lower as a result of photodegradation while the thionine signal no longer appears. This is a clear demonstration of the need for light-induced activation of the film in order to obtain chemical grafting of electroactive probes.

The average degree of thionine group grafting is estimated at 18%, with erspect to that by integration of electrical charges, of the amount of immobilised thionine compared to the amount of polymerised benzophenone.

3.2—Poly(pyrrole benzophenone)—Rabbit Antibodies (IgG)

3.2. A—Demonstration of Photofixation of Rabbit Antibodies (IgG) on a Polypyrrole-Benzophenone or PPBP Film by Measurement of Permeability Determination of the permeability of films and the kinetics of charge transfer of a redox system is based on the intensity/potential (I/E) graphs in a stationary system of oxidation or reduction at the surface of the electrode of an electroactive species. Measurements are carried out on the tips of turning electrodes at a low rate of voltage sweeping.

Measurement of the permeability of a film is based on determining the rate at which the electroactive solute diffuses across the film to be oxidised or reduced at the surface of the electrode. These measurements are thus carried out with the aid of electroactive probes of adequate size capable of passing through the film. If the film is conductive, it is necessary to work in a potential range in which the polymer is not conductive or to destroy the electroactivity of the film in order to prevent interference. The film can actually play the role of a redox mediator for oxidation or reduction of electroactive probes. This aspect partly influences the choice of probe: the redox potential of species must fall within the range in which the film is not conductive. The second criterion is the size of probes: permeability measurements are often carried out using several probes whose steric size varies.

Within the scope of this invention, the inventors have chosen to work with decamethylferrocene (DMFc), an electroactive species whose reversible oxidation takes place in organic medium at −100 mV/Ag/Ag$^+$.

The intensity as a function of potential graphs (I(E)) were obtained using rotating electrode tips made of glassy carbon coated with a PPBP film (0.5 mC (millicoulomb), before and after immersion in rabbit antibody (IgG) deoxygenated aqueous solution at a concentration of 0.5 mgml$^{-1}$ and irradiation for two hours by a 250 W mercury lamp through an IR filter with an intensity of 100 mWcm-2.

Once rinsed, the electrodes are placed in a 0.5 mM DMFc solution in acetonitrile and the oxidation current of the electrochemical probe is recorded as a function of potential at different rates of electrode rotation.

Figure 11:
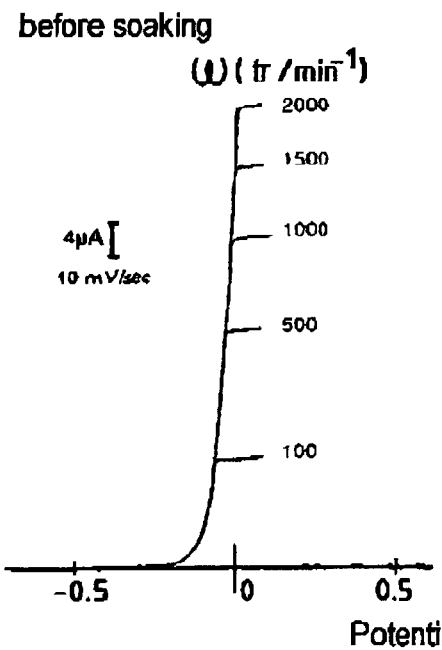
FIGS. 11 and 12 represent the intensity graphs (I) in microamperes on the ordinate by potential sweeping and $Ag/Ag^+$ redox system on the abscissa of the polypyrrole-benzophenone film before soaking or immersion in a solution (FIG. 11) in a rabbit antibody solution or after immersion and irradiation (FIG. 12).

The plots obtained are shown in FIGS. 11 (before soaking) and 12 (after soaking).

Figure 12:
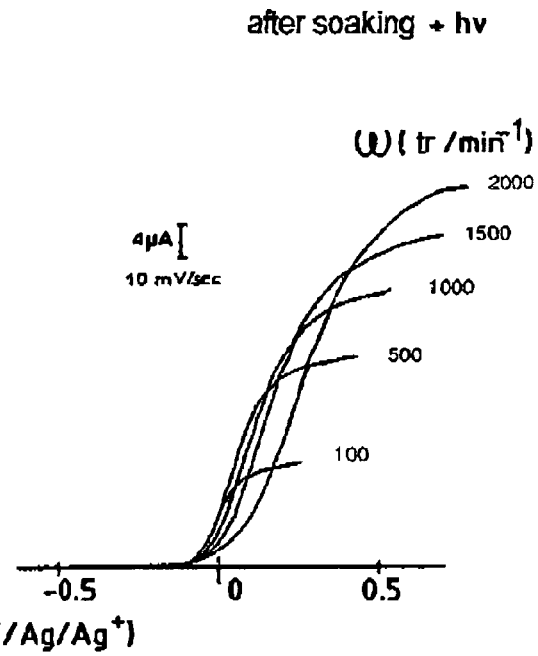

FIGS. 11 and 12 show that after soaking and irradiation, the limit diffusion currents and the oxidation potential of the probe move towards the higher values. These two phenomena can be attributed to the presence of antibodies grafted onto the surface. This modifies the mobility of the probe in the resulting film and the kinetics of charge transfer in the electrochemical process.

Figure 13:
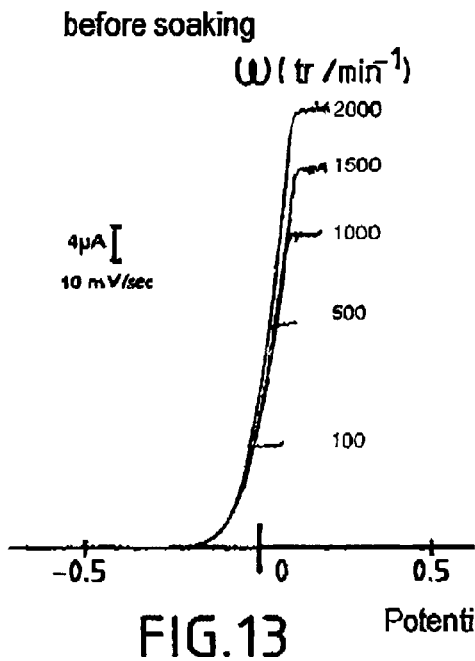
FIGS. 13 and 14 are similar graphs to FIGS. 11 and 12 respectively, without light excitation.
Figure 14:
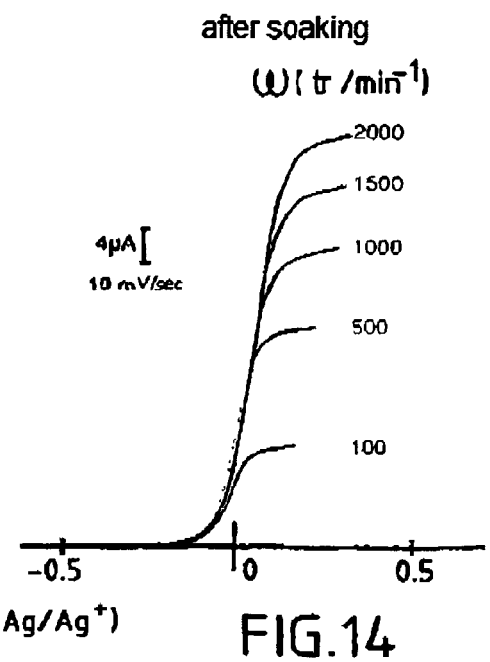

The same experiment carried out without light excitation of the immersed tips (soaking) does not lead to any significant change in the oxidation current of the electrochemical probe as shown in FIGS. 13 and 14, before soaking and after soaking or immersion respectively. This demonstrates that in the absence of light irradiation, antibodies are not fixed.

With regard to the I(E) graphs in FIGS. 11 to 14, it should be recalled that determination of permeability is conducted using Koutecky-Levich based on the following equation:

$$\frac{C_s^*}{i_{lim}} = \frac{\delta_m}{KD_m nFA} + \frac{1}{0.62 D_s^{2/3} \gamma^{1/6} nFA} * \frac{1}{\omega^{1/2}}$$

Permeability corresponds to the following ratio $$P_m = \frac{KD_m}{\delta_m}$$

| | |
|---|---|
| $C^*$ | concentration of the electroactive species in the solution |
| $\omega$ | rotation speed of the rotating electrode |
| $D_s$ | diffusion coefficient of the species in solution |
| $D_m$ | diffusion coefficient of the species in the film |
| $\delta_m$ | film thickness |
| $i_{lim}$ | limit diffusion current |
| $\gamma$ | kinematic viscosity of the solution |
| n | number of electrons exchanged during the faradic process |
| F | faraday |
| A | surface of the electrode |
| K | partition coefficient of the area between the film and solution |

The graphs represent the variation in the ratio $$\frac{C_s^*}{i_{lim}}$$

as a function of $$\frac{1}{w^{1/2}}.$$

Knowing n, F and A, the starting ordinate makes it possible to obtain the permeability value $P_m$.

$i_{lim}$ is obtained by plotting the intensity/potential graphs in stationary mode for different electron rotation speeds.

Figure 15:
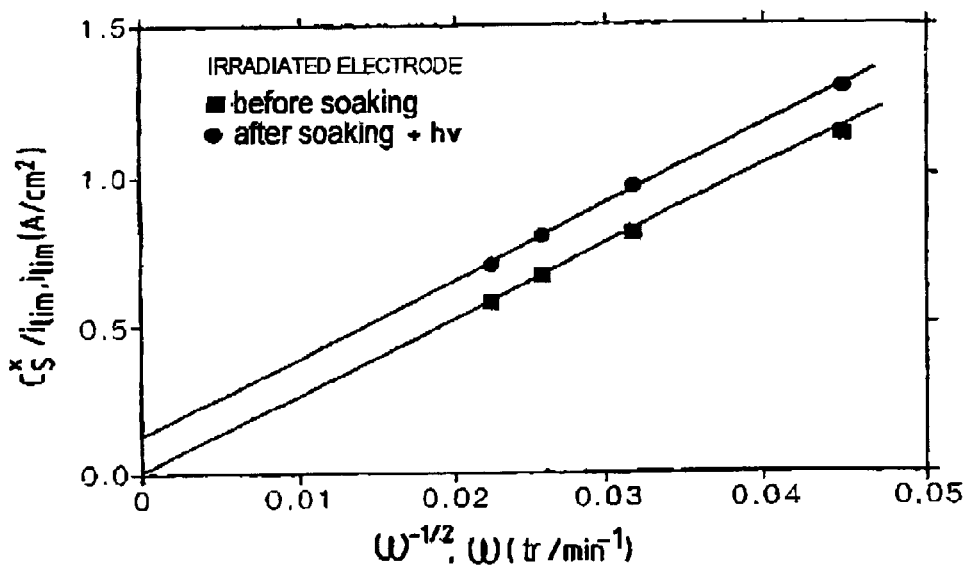
FIG. 15 represents Koutecaky-Levich graphs in which the straight line linking the square is obtained with graph I(E) of FIG. 11 and the graph linking the circles is that obtained with graph I(E) of FIG. 12 after soaking and light excitation.

Using the preceding I(E) plots gives the Koutechy-Levich graphs shown in FIG. 15 where the starting ordinate is inversely proportional to the permeability of films for the probe.

Figure 16:
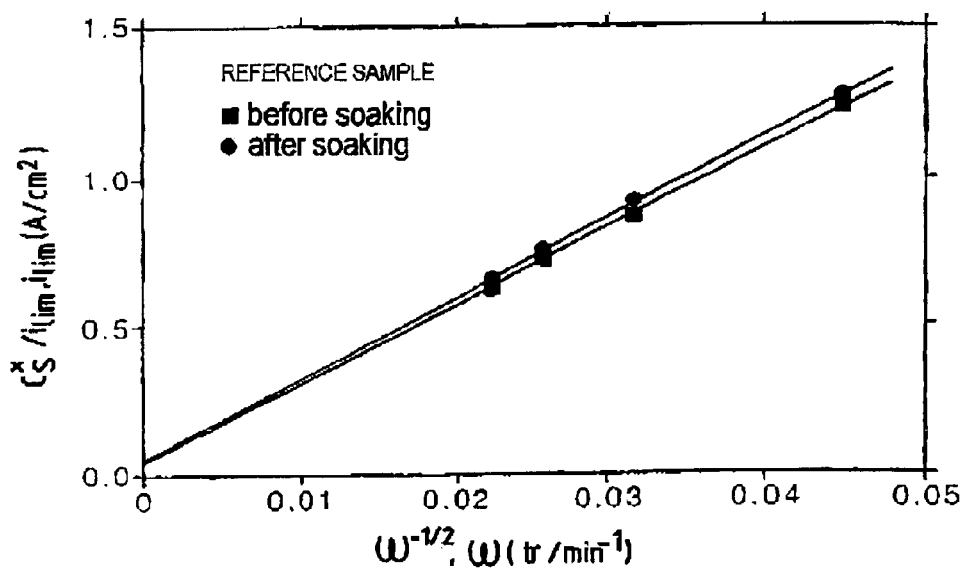
FIG. 16 is a graph similar to that in FIG. 15 but obtained with graphs I(E) in FIGS. 13 and 14 respectively, without light excitation.

FIG. 15 shows that film permeability is diminished after grafting. The same graphs obtained with I(E) plots for a non-irradiated electrode (FIG. 16) converge towards the same starting ordinate which suggests that the permeability of the film is not altered by simply soaking or immersing the electrodes in antibody solution.

3.3—Poly(pyrrole benzophenone)—ASB

Irradiation of a poly (p-pyrrole benzophenone) leads to a large decrease (54%) in the intensity of the redox system at −2 V relative to the benzophenone function. This phenomenon illustrates the disappearance of the ketone function and thus the reactivity of this group under the effect of irradiation.

As biological macromolecules are almost exclusively soluble in aqueous media, the efficacy of grafting by irradiation was tested in aqueous medium. To this end, bovine serum albumin (BSA) was used initially as a model protein. Modified electrodes were plunged in aqueous solution of this protein and irradiated with light from a 250 W mercury lamp through an IR filter with an intensity of 100 mWcm-2.

In order to detect immobilisation of proteins at the surface of the film, these electrodes were transferred to an organic electrolyte and the permeability of the film was tested using an electroactive probe (ferrorcene). A 25% reduction in initial permeability appears to confirm protein grafting. It should also be noted that this reduction is not the result of simple adsorption of the protein onto the surface of the film. The same experiment carried out without irradiation only leads to a 9% loss in film permeability.

3.4—Poly(pyrrole benzophenone)—Glucose Oxidase Enzyme

To confirm these grafting possibilities, irradiation of electrodes, modified under the conditions described in example 3.3, was carried out on another biologically active protein: an enzyme. This enzyme, glucose oxidase or GOD, catalyses oxidation of glucose into gluconic acid in the presence of dioxygen which is itself reduced to $H_2O_2$.

As $H_2O_2$ oxidises electrochemically at a potential of 0.6 V versus ECS on a platinum electrode, this enzyme reaction can be followed by an electrical signal. Consequently, the modified electrode, after irradiation, is transferred to an aqueous solution and maintained at a potential of 0.6 V vs ECS. In the presence of glucose, the enzyme forms $H_2O_2$ which is oxidised, at this potential, at the surface of the platinum electrode, thus generating an electrical current.

The amperometric response of the electrode to glucose additions demonstrates the possibility of light-induced grafting of an enzyme of this kind onto a polymer while retaining its biocatalytic activity towards its substrates.

This reaction also makes it possible to plot a glucose standard graph in which the slope of the linear section I (intensity=f(glucose concentration) gives the sensor's sensitivity: 3.37 $mAM^{-1}$ $cm^{-2}$.

The same experiment carried out without irradiation demonstrates that the enzyme can adsorb onto the polymer film but the sensitivity of the glucose obtained (0.56 $mAM^{-1}$ $Cm^{-2}$) is much lower than before. This confirms that the enzyme is grafted onto the poly (pyrrole benzophenone) film under the effect of irradiation.

3.5—Poly(pyrrole benzophenone)—Biotine

The efficacy of light-induced grafting and accessibility of the immobilised biomolecules at the electrode's surface were examined by gravimetric measurement using the avidine-biotine system.

Gold electrodes covering microscale quartz were modified by a poly (pyrrole benzophenone) film corresponding to 2 $10^{-9}$ $molecm^{-2}$. Two modified quartz pieces were contacted with an aqueous biotine solution, one irradiated and one not irradiated. As a result of strong affine interactions between biotine (a vitamin, MW 250) and avidine (a protein, MW 66000), biotine is bound to avidine rapidly. Gravimetric measurements, in the presence of an avidine solution (0.5 mg/ml), show a reduction in frequency of 200 Hz and 70 Hz for the irradiated polymer and non-irradiated polymer respectively (see FIG. 4). This corresponds to an increase in mass at the surface of the polymer of 358 ng $cm^{-2}$ in the case of irradiation and of 125 ng $cm^{-2}$ without irradiation.

Immobilisation of a compact monolayer of avidine theoretically corresponds to a mass increase of 362 ng $cm^{-2}$. It would therefore appear that irradiation induces effective grafting of avidine at the surface of the polymer leading to the latter being totally coated with the avidine monolayer. In the absence of irradiation, and thus of biotine grafting, only 34% of the polymer surface is covered with avidine.

These results also show that grafted biotine retains excellent identification properties for avidine and thus has excellent accessibility. Gravimetric measurements show that the avidine monolayer is immobilised at the polymer-solution interface at 5.48 $10^{-2}$ $mole.cm^{-2}$. As a result, at least 5.48 $10^{-12}$ $mole.cm^{-2}$ of biotine are grafted by light induction onto the surface of the polymer. Knowing that a polymer monolayer can be approximated at 8 $10^{-11}$ $mole.cm^{-2}$, this gives a minimum grafting rate of 6%.

3.2-B—Demonstration of the Light-Induced Binding of Antibodies on a poly(pyrrole-benzophenone)—PPBP Film by Cyclic Voltammetry Glassy carbon tips coated with a PPBP film (0.5 mC) were immersed in a rabbit antibody solution (IgG), previously deoxygenated by argon bubbling for 30 minutes and irradiated by a 250 W mercury lamp for two hours.

Cyclic voltammetry of Em in solution in DMFc (0.5 mM) were recorded before and after immersion or soaking.

Figures 17, 18:
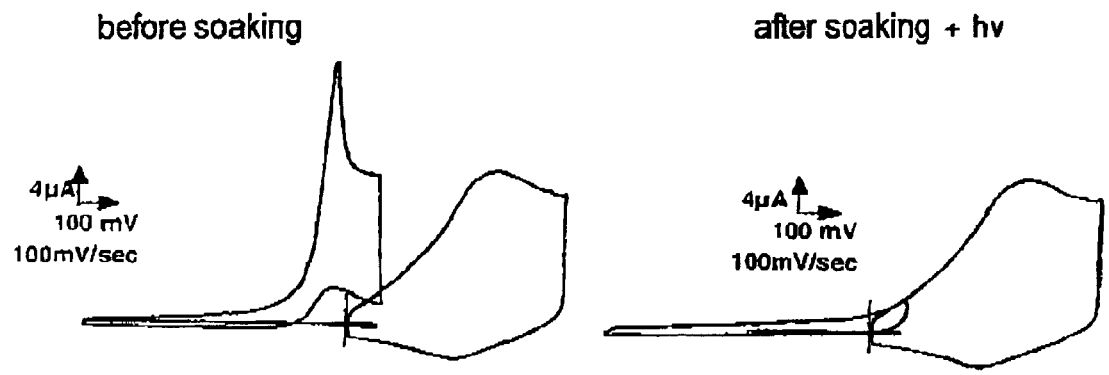
FIGS. 17 and 18 represent the electrochemical signals of the polypyrrone-benzophenone before soaking (FIG. 17) and after soaking and irradiating (FIG. 18) in rabbit antibody solution (rabbit IgG).

The graphs obtained are given in FIGS. 17 and 18.

It can be seen from FIGS. 17 and 18 that the voltammograms show typical polypyrrole film electroactivity in the positive potential range and irreversible oxidation of DMFc in the negative potential range.

This signal disappears completely after grafting of the film by rabbit IgG antibodies.

Figures 19, 20:
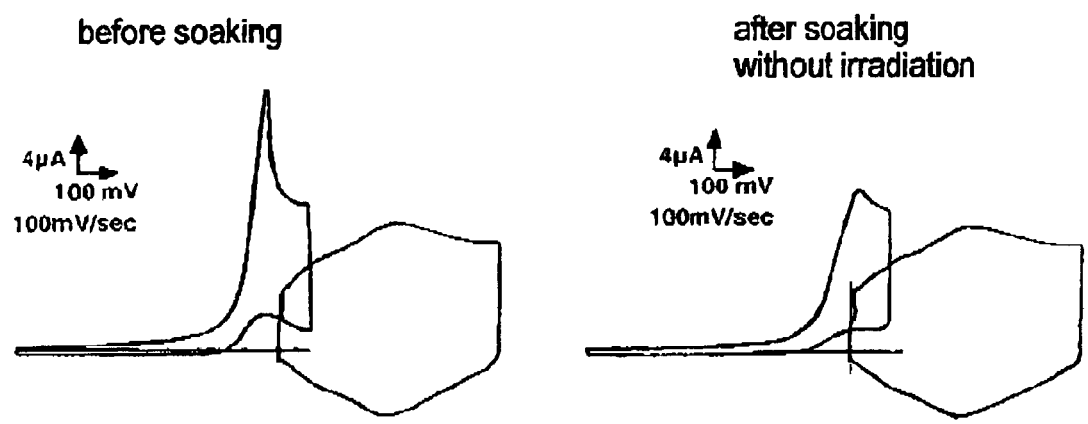
FIGS. 19 and 20 represent the graphs before soaking (FIG. 19) and after soaking without irradiation (FIG. 20) under the same conditions as those in FIGS. 17 and 18, as a comparison to demonstrate that the modification in electrochemical signals Dem in solution is less than for a non-irradiated electrode.

The modification in the electrochemical signal of Em in solution in DMFc is less for a non-irradiated electrode, as is seen by the graphs obtained without irradiation and shown in FIGS. 19 and 20.

It is found that the probe's oxidation current is slightly diminished whereas it disappears entirely for an irradiated electrode.

The set of results obtained tends to prove that immobilisation of different molecules at the surface of PPBP films is possible. This immobilisation, however, requires light-induced excitation of the films.

Simple soaking does not lead to any changes.

This product therefore has no adsorption type interaction but rather light-induced activation of covalent bonds.

Section II—Preparation of Different Electropolymerisable Monomers Functionalised by Light-Activated Groups of Benzophenone Example 4

Monomers of the phenol-benzophenone Type, for Example by 4-(2-aminoethyl)phenol(tyramine)—Benzophenone in this Case The formula for this recently synthesised monomer is as follows:

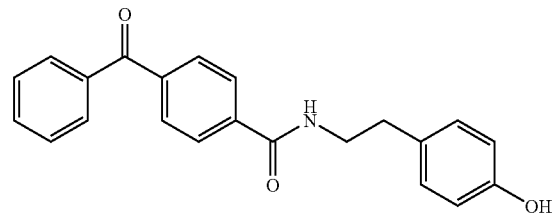

4.1—Synthesis of a New Derivative 452 mg of 4-benzoylbenzoic acid (2 mmoles), 412 mg of 1.3 dicyclohexylcarbodiimide (DCC) in 20 ml of $CH_2Cl_2$ are placed in a 50-ml flask under argon and the mixture is stirred for 5 minutes.

264 mg (2 mmoles) of 4-(2-aminoethyl) phenol or tyramine are then added and the mixture is stirred for 5 minutes.

Next, 80 mg of dimethylaminopyridine (DMAP) are added and stirring is continued for 5 days.

50 ml of water are added then extraction is carried out 3 times with 50 ml of $CH_2Cl_2$. $CH_2Cl_2$ is then evaporated and the product obtained is washed with water.

4.3—Analysis of the Product Obtained

After evaporation to dryness, NMR analysis of the product obtained shows that it consists of a mixture of two main products, the phenol derivative of benzophenone with the formula given above and a subproduct with the following formula:

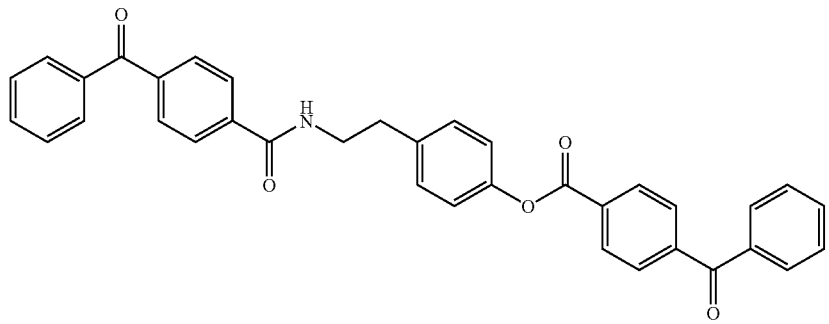

Separation of these two products is carried out by chromatography on a silica column with dichloromethane/hexane/methanol 90/5/5 by volume as the eluent.

Figure 21:
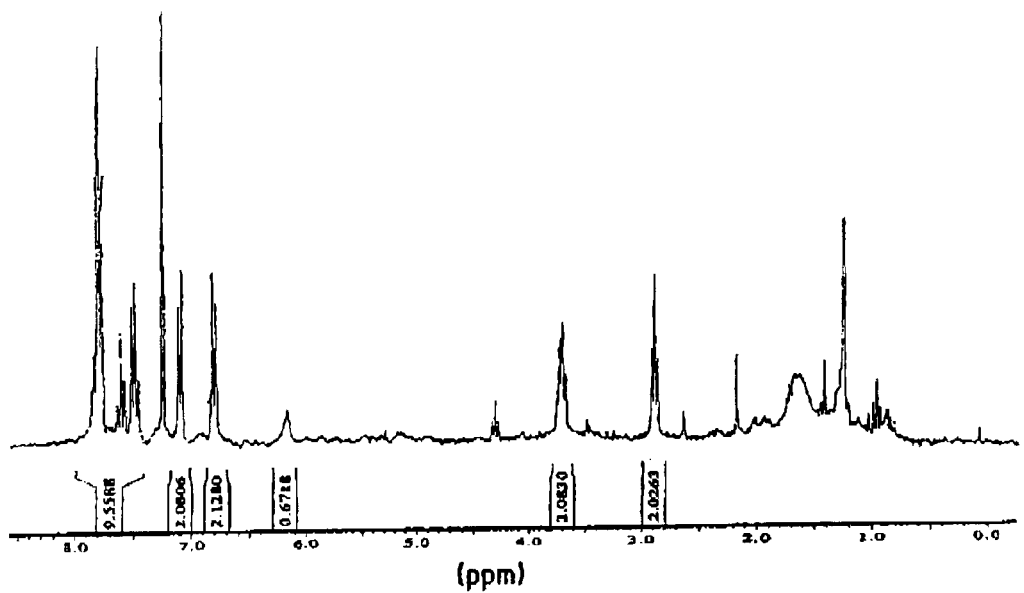
FIG. 21 represents the NMR spectrum of the 4-(2-aminoethyl)phenol-benzophenone monomer.

The NMR spectrum of 4-(2-aminoethyl)phenol-benzophenone is given in FIG. 21.

167 mg of the desired product of the invention are obtained, corresponding to a yield of 22% mole.

4.4—Electrochemistry and the Manufacture of poly-[4-(2-aminoethyl)-phenol]benzophenone Polymer The electrochemical properties of the 4-(2-aminoethyl) phenol-benzophenone monomer were analysed by cyclic voltammetry on a glassy carbon tip.

The monomer is placed in solution in methanol containing 0.1M of NaOH and 0.1M of LiCO$_4$.

Figure 22:
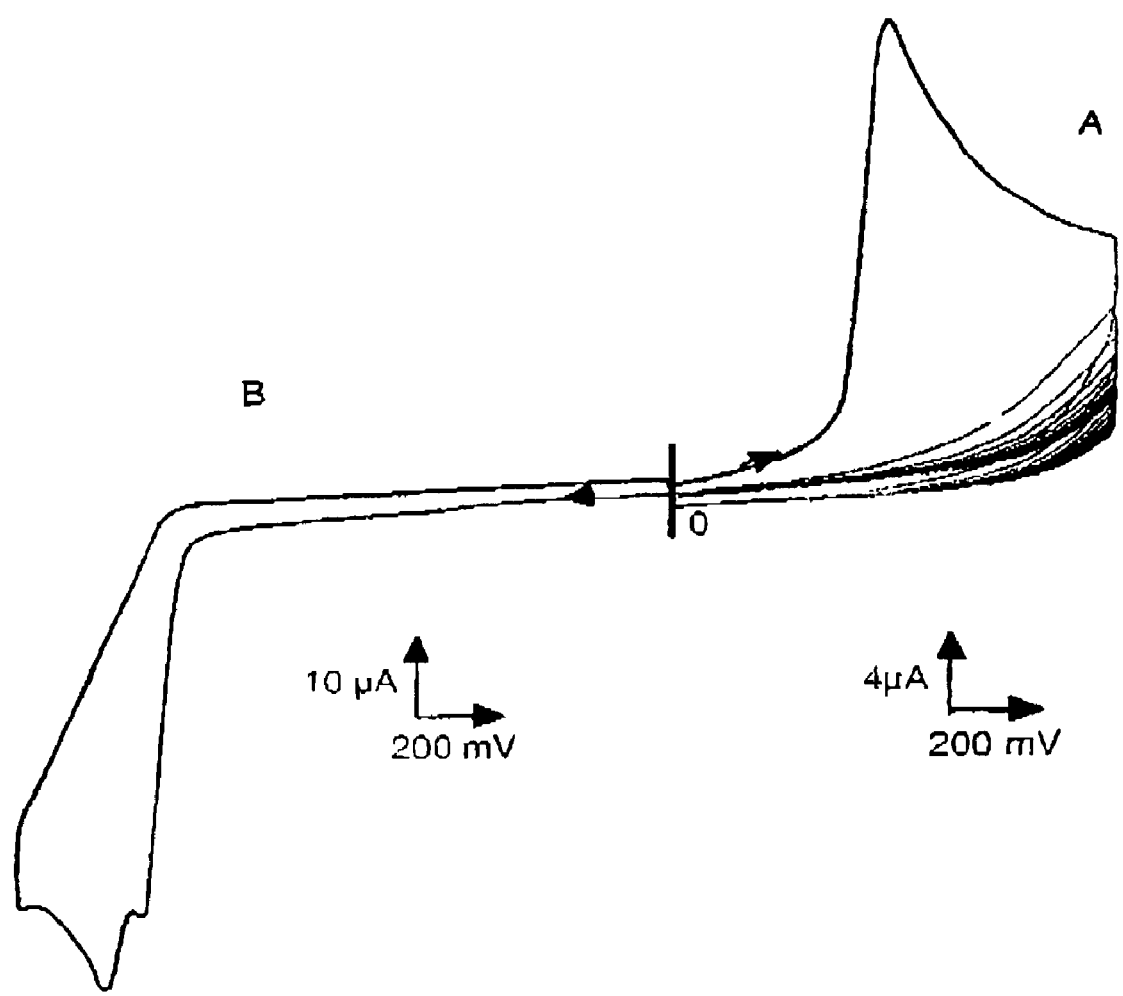
FIG. 22 represents (graph A) the electrochemical signal of the monomer in example 4 with the NMR spectrum in FIG. 21 in the course of successive potential sweeps between 0 and 1 Volt in an Ag—AgCl redox system and graph B represents the signal obtained by reduction cycling in the same monomer solution.

FIG. 22 represents (graph A) the electrochemical signal of the monomer in the course of repeated potential sweeping between 0 and 1 V relative to Ag—AgCl.

In the course of the first sweeping, a strong irreversible anode peak is observed at 0.4V corresponding to oxidation of phenol groups.

In the following cycles, the signal diminishes then disappears.

This phenomenon results from the formation at the surface of the electrode of an isolating polyphenol group, result of the polymerisation of electrogenerated radicals.

Prior to this polymerisation, FIG. 22 represents (graph B) the signal obtained by reduction cycling in the same monomer solution. An irreversible cathode peak corresponding to reduction of benzophenone groups is observed.

Figure 23:
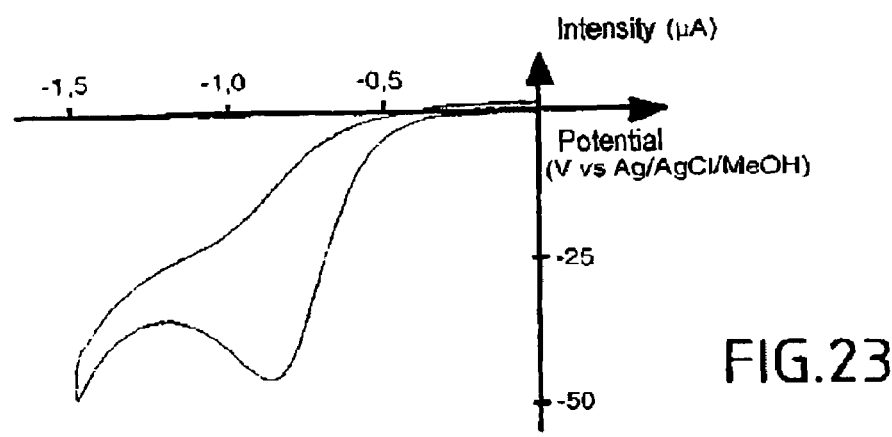
FIG. 23 represents the intensity/potential graph obtained after repeated potential sweeping between 0 and 1 Volt of an electrode transferred into an electrolytic solution devoid of monomer in the benzophene electroactivity zone.

After repeated potential sweeping between 0 and 1 V, the electrode is transferred to a monomer-free electrolyte solution and is cycled in benzophenone's electroactivity range to obtain a graph for intensity (I) relative to potential V or E (V or E represented in FIG. 23).

As FIG. 23 shows, an irreversible cathode peak corresponding to the reduction of benzophenone groups is observed which demonstrates the presence of the latter at the electrode surface and hence the formation of a polymer film.

These results also show that it is possible to electrogenerate, by electrochemical cycling, polyphenol films substituted by benzophenone groups at the surface of an electrode.

Moreover, contrary to the polypyrrole films described in examples 1 to 3, the polyphenol films in example 4 are isolating.

Example 5

Light-Induced Grafting of Biomolecules on the Electropolymers of Example 4.4 Capable of Being Grafted by Light Induction 5.1—Grafting of the Enzyme Glucose Oxidase The conditions for light-induced grafting of an enzyme onto the surface of a polymer are identical to those employed for the polypyrrole benzophenone film in example 3 above.

The electrodes are immersed and irradiated for two hours in a deoxygenated glucose oxidase solution (2 mg/ml).

The activity of the enzyme immobilised at the surface of the electrodes was measured by a conventional spectrophotometric method for oxidases.

Enzyme oxidation of glucose by glucose oxidase (abbreviated to GOD) leads to the formation of H2O2.

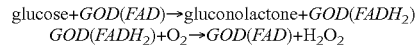

In the presence of raifort's peroxidase (HRP), H$_2$O$_2$ enzymatically oxidises ortho-toluidine.

This chromogenic species is oxidised to give a chromophor product which absorbs at 425 nm.

The variation in ortho-toluidine absorbance is followed as a function of time and converted to enzyme activity.

The spectra show a linear section for which the limiting step is the production of H2O2 by glucose oxidase.

The latter is placed in glucose saturating conditions, the slope of the linear section representing the maximum rate of enzyme catalysis.

To determine the enzyme activity of the modified electrode, the latter is immersed in a LiClO$_4$ solution (0.1M, pH 6.8) containing 250 mM of glucose, 2 U/ml of peroxidase and 0.2 mM of o-toluidine.

Figure 24:
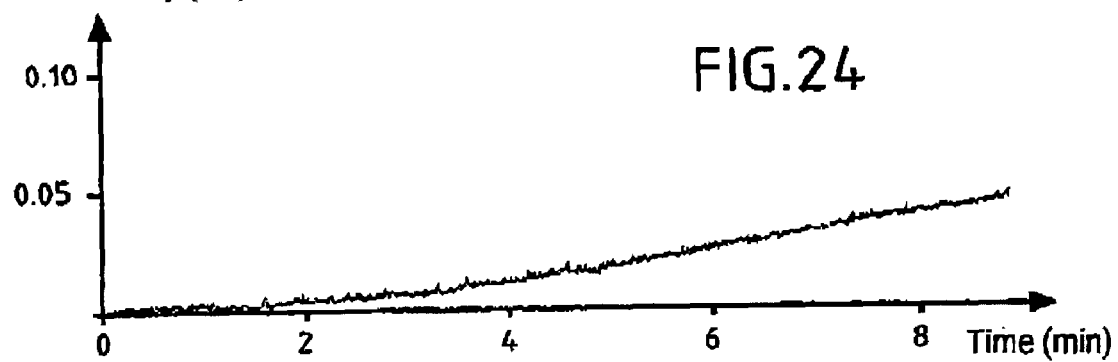
FIG. 24 represents the graph for absorbance as a function of time at 425 nm of the enzyme activity of an electrode coated with a polypyrrole-benzophenone film on which glucose oxidase is grafted according to example 5.1 below in order to show the conservation of enzyme activity on the modified electrode.

Absorbance as a function of time at 425 nm of the reaction medium is measured continuously and gives the graph shown in FIG. 24, with time in minutes on the abscissa and absorbance in the form of optic density (OD) on the ordinate.

It can be seen from FIG. 24 that the slope of the linear section is equal to 6m OD.min$^{-1}$, which corresponds to enzyme activity of 68 mU for the modified electrode.

This enzyme activity is a demonstration of the possibility of light-induced immobilisation of a protein on a polyphenol film functionalised by benzophenone groups.

Example 6

Preparation of Monomers and Polymers of the indole-benzophenone Type Conjugated to Light-Activated Groups and Grafting by Light-Induced Activation Preparation of the 3-(2-aminoethyl)indole-benzophenone monomer is carried out.

6-1—Formula of this New Compound

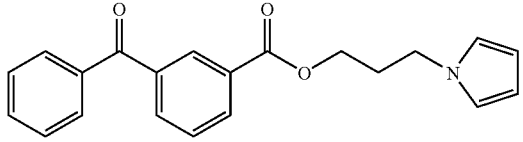

6-2—Synthesis of the New Compound 452 mg of 4-benzoylbenzoic acid (2 mmoles), 412 mg of DCC in 20 ml of CH$_2$Cl$_2$ are placed in a 50-ml flask under argon and the mixture is stirred for 30 minutes.

320 mg (2 mmoles) of 3-(2-aminoethyl)indole or tryptamine are then added and the mixture is stirred for 5 minutes.

Next, 80 mg of DMA are added and stirring is continued for 1 week.

50 ml of water are added then extraction is carried out 3 times with 50 ml of CH$_2$Cl$_2$. The organic phase is dried on Na2SO4 then the solvent is evaporated in a rotary evaporator under reduced pressure and washing with ethanol then chromatographied on silica (dichloromethane/hexane/methanol : 86/10/4 by volume) are carried out.

The yield of the product having the formula given in 6.1 is 68% by mole.

6-3—NMR Analysis

Figure 25:
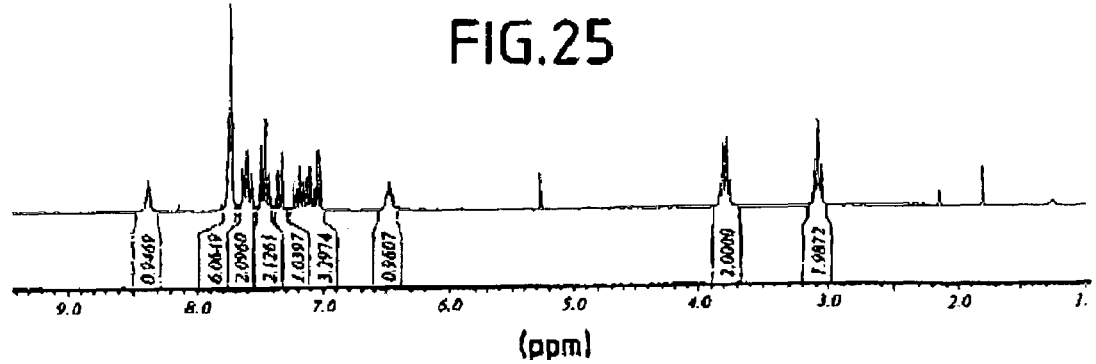
FIG. 25 represents the NMR spectrum of the 3-(2-aminoethyl)indol-benzophenone monomer in examples 6.1 and 6.2.

Conventional NMR analysis is carried. The NMR spectrum is given in FIG. 25.

6-4—Electrochemistry of the Preparation of polyindole-benzophenone Polymer

In the same way as in the previous examples, an electrochemical study using cyclic voltammetry is carried out on the monomer (2 mM) in acetonitrile which shows a pre-peak at 0.9V followed by an irreversible anodic peak at 1.16V corresponding to irreversible oxidation of the indole group.

In reduction, a system of reversible peaks is seen at $E_{1/2}=-1.8V$.

This redox system corresponds to reduction of the benzophenone group.

The surface of the electrode is modified by electrolysis at a control potential of 0.8V or by repeated potential sweeping in the range of 0–0.9V.

After transfer to an acetonitrile solution, the voltammogram of the modified electrode has a reversible system at $E_{1/2}=-0.6V$ due to the electroactivity of the polyindole film as well as a reversible system at $E_{1/2}=1.8V$ corresponding to immobilised benzophenone groups.

This shows the formation of a polyindole polymer film containing benzophenone groups.

Consequently, functionalisation of benzophenone by an electropolymerisable indole group makes it possible to obtain polyindole polymer films by electro-oxidation.

Example 7

Preparation of Monomers and Polymers of the Vinyl-Benzophenone Type Conjugated to Light-Activated Groups and Grafting by Light-Induced Activation As an example of the vinyl-benzophenone monomer, vinylaniline-benzophenone monomer was carried out.

7-1—Formula of this New Compound

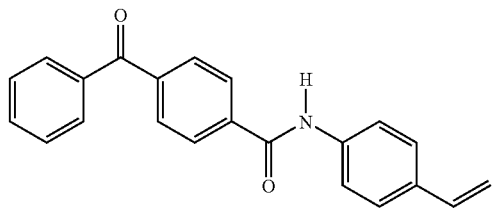

7-2—Synthesis of this New Compound 452 mg of 4-benzoylbenzoic acid (2 mmoles), 412 mg of DCC in 20 ml of CH$_2$Cl$_2$ are placed in a 50-ml flask under argon and the mixture is stirred for 30 minutes.

267 mg (2.2 mmoles) of vinylaniline and the mixture is stirred for 5 minutes.

Next, 80 mg of DMA are added and stirring is continued for 5 days.

50 ml of water are added then extraction is carried out 3 times with 50 ml of CH$_2$Cl$_2$. The organic phase is dried on Na2SO4.

Chromatography is carried out on silica (dichloromethane/hexane/methanol : 86/10/4 by volume) and the product, vinylaniline-benzophenone having the formula given in 7.1, is isolated at a yield of 22%.

7-3—NMR Analysis

Figure 26:
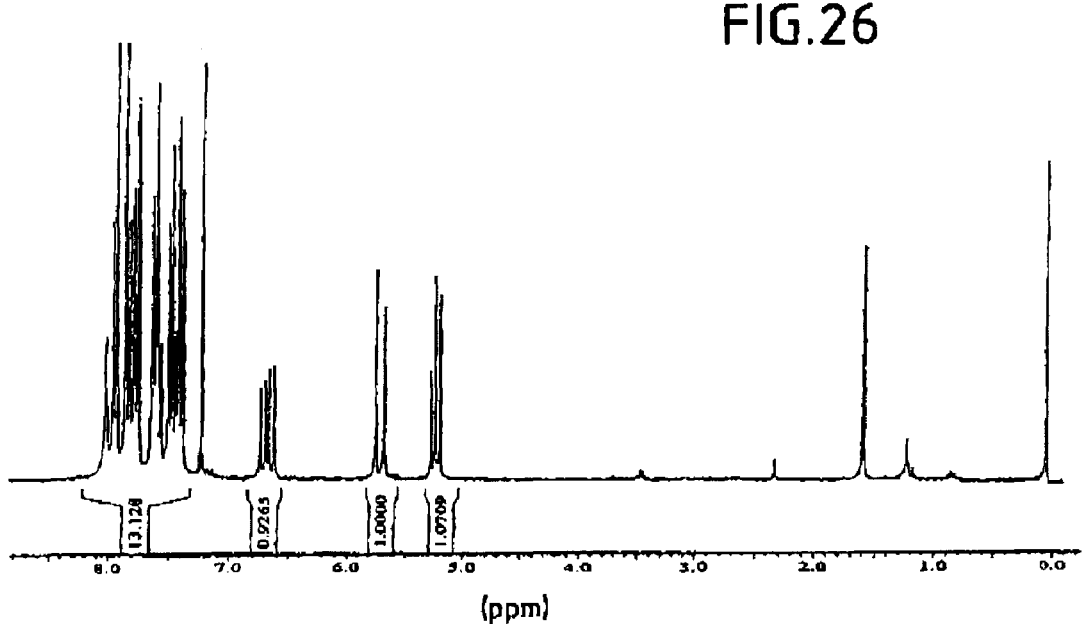
FIG. 26 represents the NMR spectrum of the vinylaniline-benzophenone monomer in examples 7.1 and 7.2.

Conventional NMR analysis is carried. The NMR spectrum is given in FIG. 26.

7-4—Electrochemistry of the Preparation of polyvinyl-benzophenone Polymer

In the same way as for the polymers generated in the previous examples, the voltammogram of vinyl-benzophenone (2 mmoles in acetonitrile) clearly shows, in the negative potential range, an irreversible cathode peak at −1.88V corresponding to reduction of the benzophenone group.

This reduction is followed by electronic transfer leading to the formation of a vinyl radical at the site of polymerisation.

Repeated potential sweeping in the 0–2.4V range leads to the formation of a polyvinyl benzophenone polymer film at the surface of the electrode.

In addition to the electroactivity of benzophenone, the modified electrode exhibits a system of almost-reversible peaks around −0.15V resulting from the electroactivity of the functionalised polyvinyl film.

Consequently, functionalisation of a light-activated group by the vinyl group constitutes another method for electrochemcial polymerisation of benzophenones in the form of polyvinyl films.

Section III—Preparation OF Monomers then Polymers Including Other Light-Activated Groups The azide group is given as an example of other light-activated groups.

In a preferred example, the azide group is functionalised with a pyrrole as the electropolymerisable group.

Example 8

Preparation of a Monomer of the Azidopyrrole Type, for Example 4-Fluoro-3-Nitro-Phenylazide-Pyrrole 8.1—Formula of this New Compound The formula of this new compound is given below:

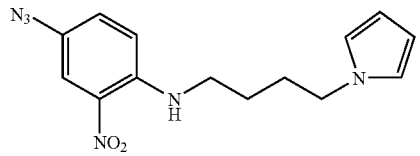

8.2—Synthesis of this new Compound in Darkness 207 mg of aminobutylpyrrole (1.5 mmoles) in 5 ml of dry THF are placed in a 25-ml flask. 250 mg (1.37 mmoles) of 4-fluoro-3-nitro-phenylazide in 5 ml of dry THF are added, the mixture is stirred for 30 minutes. THF is evaporated and the precipitate obtained is dissolved in 7 ml of $H_2O$. 7 ml of NaOH 1 M are then added.

Extraction with 2×15 ml of ethyl acetate is then carried out. The ethyl acetate solution is then dried on $Na_2SO_4$ and chromatographied under the same chromatographic conditions as in the previous examples to obtain a product having the formula given in 8.1 at a yield of 54% by mole.

8.3—NMR Analysis

Figure 27:
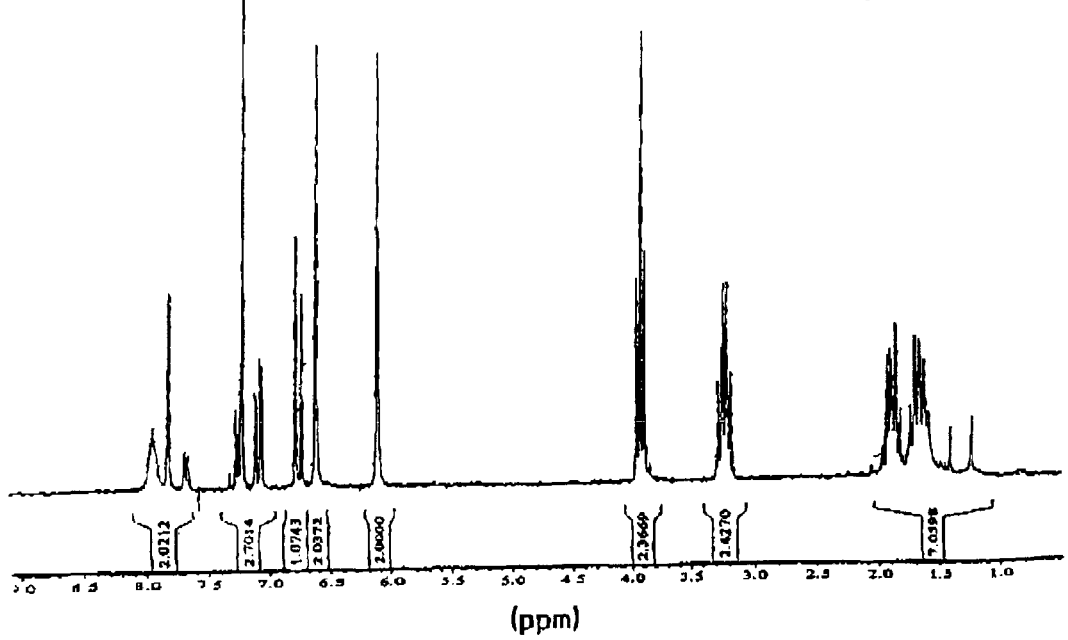
FIG. 27 represents the NMR spectrum of the 4-fluoro-3-nitrophenylazide-aminobutylpyrrole monomer in examples 8.1 and 8.2.

After chromatography, the purity of the product obtained and its chemical formula were confirmed by NMR. The NMR spectrum is shown in FIG. 27.

Figure 28:
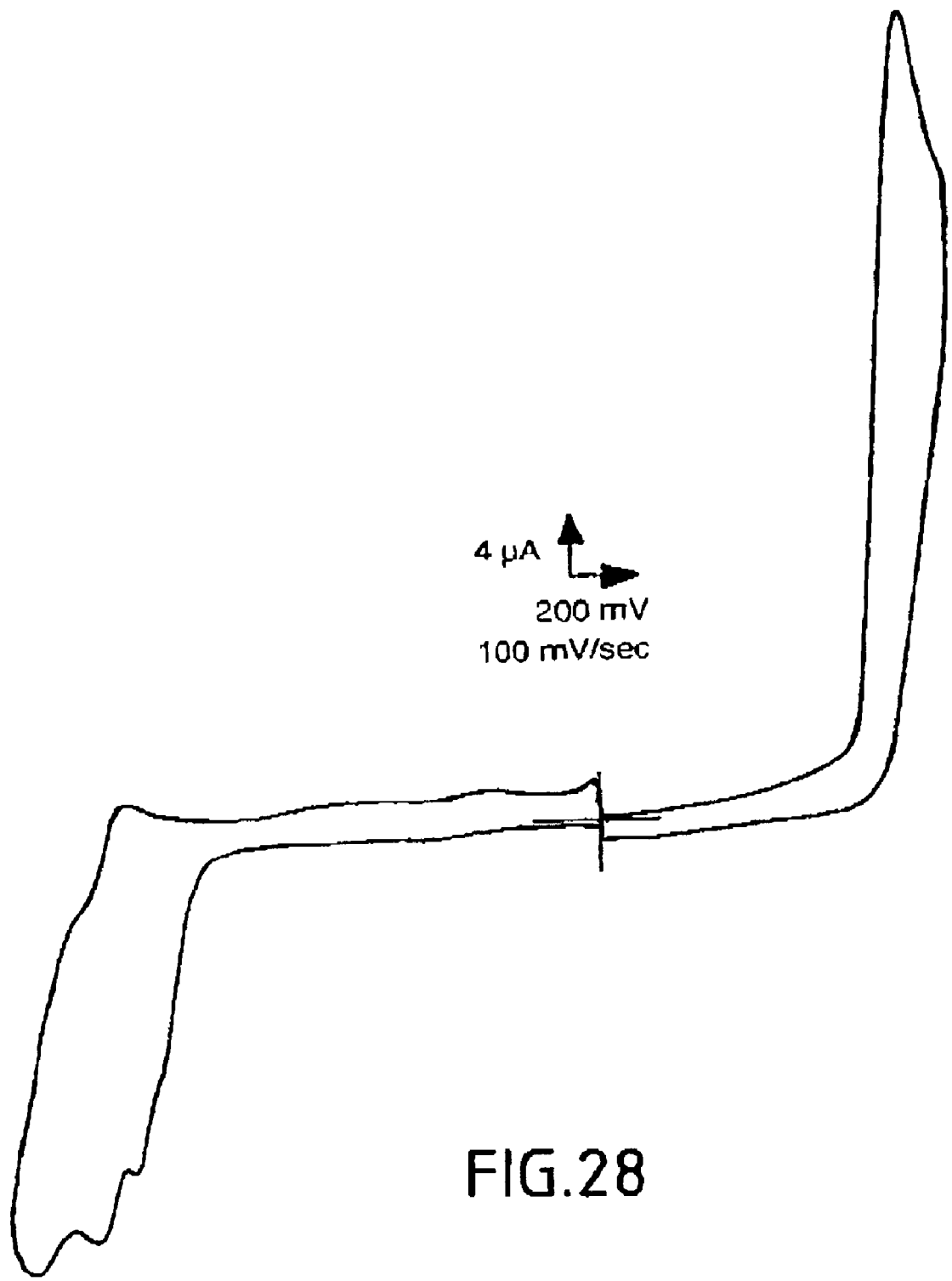
FIG. 28 represents the polymerisation voltammogram of the monomer whose NMR spectrum is shown in FIG. 27, showing an irreversible peak in the anode at +0.95 V/Ag/Ag$^+$ corresponding to oxidation of the pyrrole group.

8.4—Electrochemistry of the Synthesis of Polypyrrole Polymer Including a Light-Activated Azide Group The electrochemical properties of the monomer were analysed by cyclic voltammetry on a glassy carbon tip. The monomer is dissolved in acetonitrile (1.5 mM) away from light. As can be seen from FIG. 28, the anode area of the voltammogram shows an irreversible peak at +0.95 V/Ag/$Ag^+$ corresponding to oxidation of the pyrrole group.

In the cathode region, several waves of irreversible reduction (−1.4; −1.5 and −1.7 V/Ag/$Ag^+$) occur, possibly corresponding to successive reductions of the nitro group.

The formation of pyrrole films was carried out by successive potential sweeping between 0 and 0.90V/Ag/$Ag^+$. This formation is illustrated by the appearance and development of a redox system at +0.4V/Ag/$Ag^+$, characteristic of the electroactivity of polypyrrole chains and the graph obtained is shown in FIG. 29 (graph A).

The films can also be formed by controlled-potential electrolysis (0.9V/Ag/$Ag^+$). The graph obtained is given n FIG. 30 (graph B) which shows the electrode signal after electro-oxidation of 2 mC and its transfer to a monomer-free electrolyte solution. The voltammogram for this electrode clearly demonstrates the characteristic electroactivity of the pyrrole film in the anode region.

These initial results show that it is possible to electrogenerate polymer films at the surface of an electrode using an azidopyrrole monomer organic solution. The reproducible films obtained are hydrophobic, resistant and of adjustable thickness.

8.5—Grafting of a Biological Entity, for Example the Enzyme Glucose Oxidase (GOD)

The azides, preferably arylazides, used as benzophenone groups are precursors of light-induced radical generation.

By photolysis, the formation of highly-reactive nitrene intermediates results in the formation of covalent bonds between the photogenerated intermediate and the biomolecule.

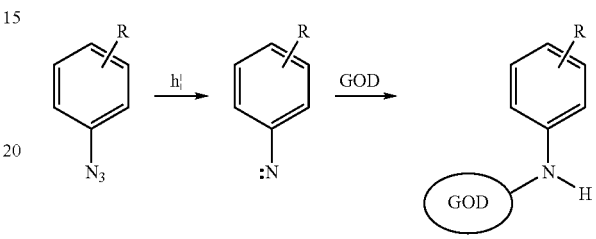

Polypyrrole films were formed by electrolysis (2 mC) at a given potential value on a platinum electrode. The polymers obtained, protected from light, were transferred to a 1 mg/ml glucose oxidase aqueous solution (GOD) and irradiated for two hours with light (300–350 nm) from a 250 W mercury lamp.

8.5—A Measurement of the Enzyme Activity of Irradiated Electrodes

After rinsing the electrodes, their enzyme activity was determined according to the method used for electrodes modified by polypyrrole benzophenone.

The slope of the linear part of the absorbance versus time graph for otoluidine is equal to 0.38 mOD/min. which corresponds to an enzyme activity of the electrode equivalent to 22 mU/$cm^2$. This enzyme activity of the polypyrrole film functionalised by azido groups demonstrates the presence of enzyme molecules immobilised by light-induced grafting.

8.5—B Glucose Assay

Amperometric assays of glucose were undertaken in aqueous medium using grafted electrodes at +600 Mv/Ag/AgCl to oxidise enzymatically generated $H_2O_2$ molecules at the surface of the electrodes. The glucose standard graph is given in FIG. 31.

Figure 31:
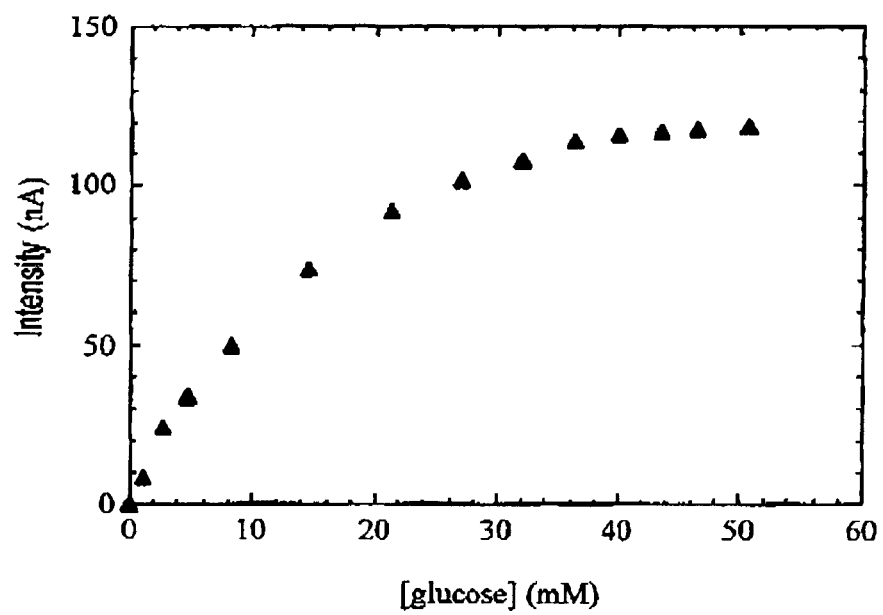
FIG. 31 represents a glucose calibration graph in aqueous medium with an electrode coated with a poly[aminobutylpyrrole] polymer film including 4-fluoro-3-nitro-phenylazide groups obtained by polymerisation of the monomer in example 8.2, under the conditions described for example 8.3 and onto which the enzyme glucose oxidase is grafted under the conditions of example 8.4, in aqueous medium at +600 mV/Ag/Ag$^+$ in order to oxidise enzymatically generated H$_2$O$_2$ molecules at the surface of the electrode as indicated within the scope of example 8.4

As can be seen from FIG. 31, the amperometric response of the electrode modified by addition of glucose shows a linear section of the slope equal to 40 µA/M/$cm^2$ for a concentration below 8 mM. Above this concentration, the graph inclines towards a value corresponding to the biosensor's maximum current ($I_{max}$=120 nA) when the enzymes are saturated with substrates.

8.4-C Lineweaver-Burk Representation

The shape of the calibration graph obtained is similar to that of the graph for Michaelis-Menten type enzymatic catalysis. Given that the enzyme step in the enzymatic process for substrate detection the is limiting, the amperometric response can be likened to the enzyme reaction rate. In this hypothesis, a model of the biosensor is obtained using the Lineweaver-Burk representation.

$$\frac{1}{I} = \frac{1}{I_{max}} + \frac{K_m^{app}}{I_{max}}\frac{1}{C}$$

in which:

I: intensity of the biosensor's amperometric response $I_{max}$: maximum intensity of the biosensor's amperometric response in the presence of a saturating substrate concentration $K_m^{app}$: Michaëlis apparent constant, characteristic of biomaterials C : glucose concentration As can be seen from FIG. 22, this model makes it possible to obtain the Michaelis-Menten apparent constant, i.e. $K_m^{app}$.

Figure 32:
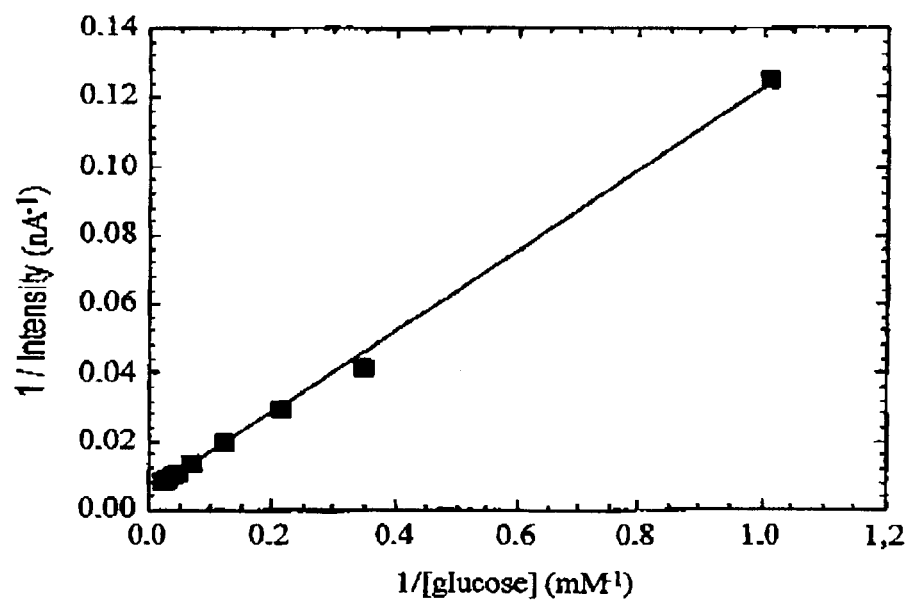
FIG. 32 represents a Lineweaver-Burk calibration graph with reverse intensities in nanoampere$^{-1}$ on the ordinate and reverse glucose concentration in millimole$^{-1}$ on the on the abscissa allowing the Michaelis Menten apparent constant to be accessed, equal to 20 mM in this case, similar to that of the kinetic constant of the free glucose oxidase enzyme in solution.

$K_m^{app}$ obtained is equal to 20 mM as can be seen in FIG. 32 and is similar to the kientic constant for the enzyme free in solution. This similarity in values shows the low limitations of light-induced grafting of enzymes onto the surface of a polymer with respect to enzymes encapsulated within the material.

This set of results shows the efficacy of light-induced grafting of molecules by irradiation of electropolymerised azide sites.

It therefore appears that the pyrrole site makes it possible to obtain, by controlled-potential electrolysis, a hydrophobic polymer film that is resistant and of adjustable thickness, functionalised by azide groups which retain their ability to undergo light-induced grafting by irradiation.

What is claimed is:

1. Pyrrolbenzophenone monomer of formula:

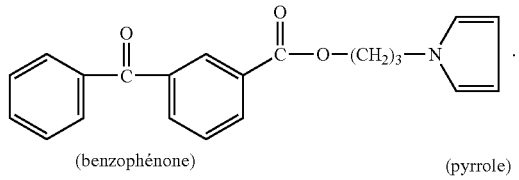

(benzophénone)    (pyrrole)

* * * * *